United States Patent
Suhami

(10) Patent No.: US 10,610,122 B2
(45) Date of Patent: Apr. 7, 2020

(54) LINEAR VELOCITY IMAGING TOMOGRAPHY

(71) Applicant: Avraham Suhami, Petach Tikva (IL)

(72) Inventor: Avraham Suhami, Petach Tikva (IL)

( * ) Notice: Subject to any disclaimer, the term of this patent is extended or adjusted under 35 U.S.C. 154(b) by 844 days.

(21) Appl. No.: 14/987,828

(22) Filed: Jan. 5, 2016

(65) Prior Publication Data

US 2017/0188874 A1 Jul. 6, 2017

Related U.S. Application Data

(60) Provisional application No. 62/234,412, filed on Sep. 29, 2015.

(51) Int. Cl.
*A61B 5/00* (2006.01)
*A61B 5/05* (2006.01)

(52) U.S. Cl.
CPC .................. *A61B 5/0507* (2013.01)

(58) Field of Classification Search
CPC ......... A61B 6/00; A61B 5/708; A61B 5/0507; A61B 5/4547; A61B 5/4381; A61B 5/4312; A61B 5/0044; A61B 5/0042; A61B 2562/0228; A61B 5/7246; A61B 5/0402

See application file for complete search history.

(56) References Cited

U.S. PATENT DOCUMENTS

| 9,268,014 | B2* | 2/2016 | Rothberg | A61B 8/4254 |
| 2006/0239404 | A1* | 10/2006 | Udpa | A61B 6/032 378/62 |
| 2015/0065860 | A1* | 3/2015 | Shvartsman | G01R 33/3806 600/411 |

OTHER PUBLICATIONS

Charvat et al, Time-of-flight Microwave Camera, Oct. 5, 2015; Published in Nature, Scientific reports 5, article # 14709. 2015.*

* cited by examiner

*Primary Examiner* — Joel Lamprecht

(57) ABSTRACT

The invention describes a new Imaging modality based on Linear Velocity Imaging Tomography; its applications include differentiating between malignant and benign tissues, the ability to correlate an ECG trace with actual disorders of the heart and Imaging Brain communications.

19 Claims, 14 Drawing Sheets

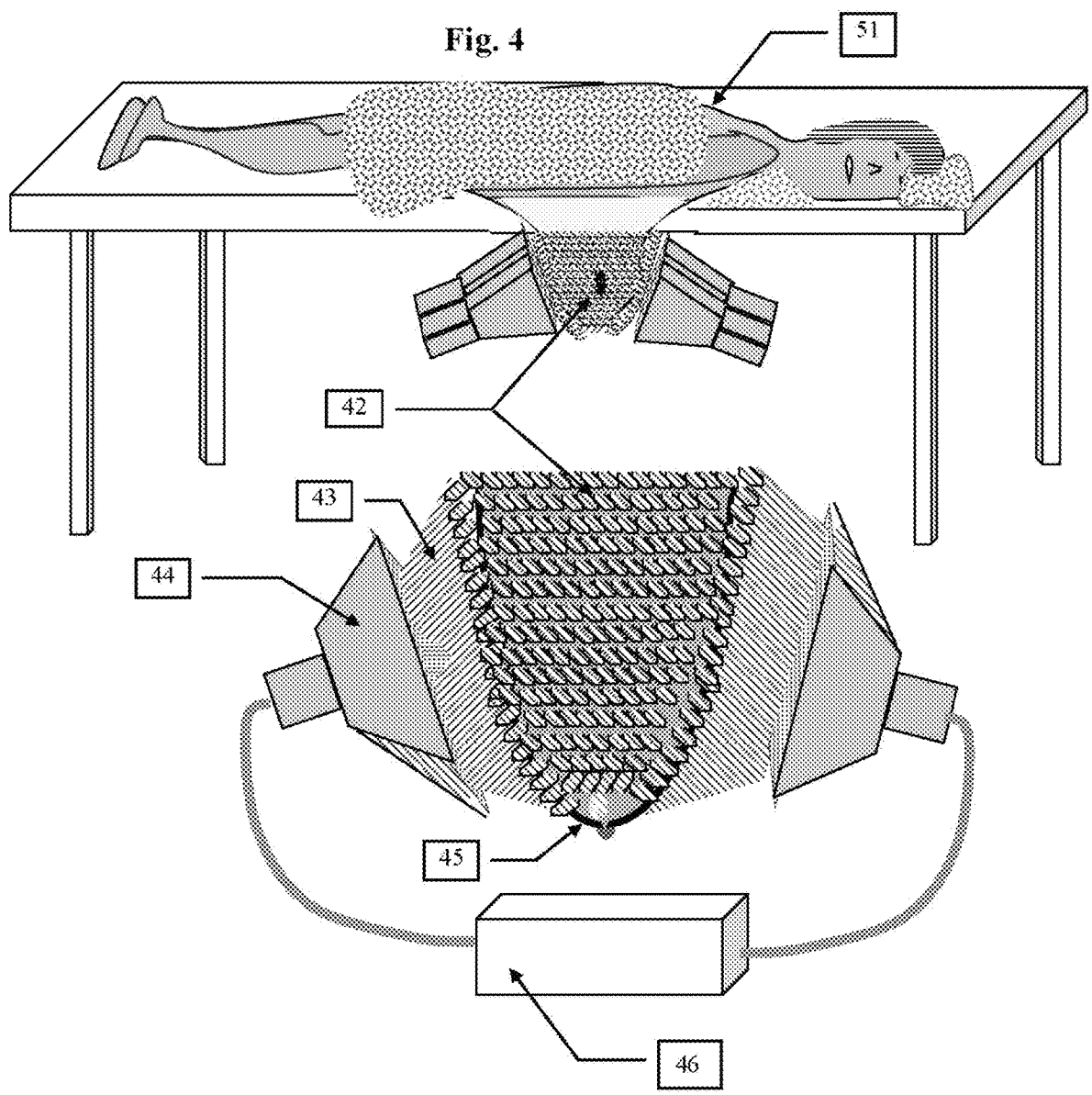

Fig. 7
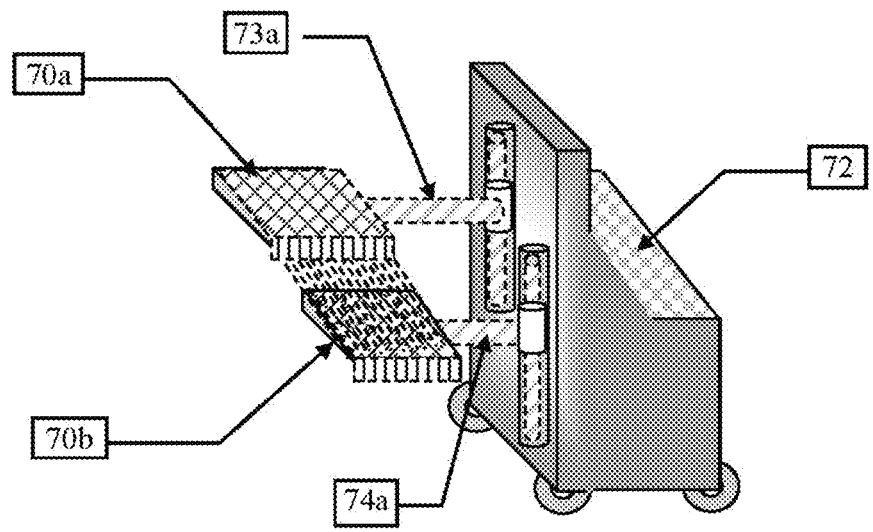
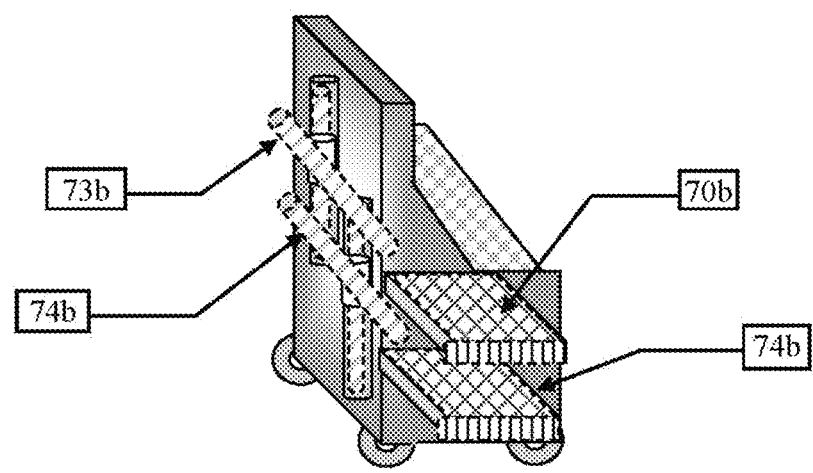

image from https://en.wikipedia.org/wiki/Giant_cell

LINEAR VELOCITY IMAGING TOMOGRAPHY

This application claims priority benefit of provisional utility application No. 62/234,412 titled "Linear Velocity Imaging Tomography filed on 2015, Sep. 29.

FIELD OF THE INVENTION

This invention relates to a new modality of Imaging where velocity changes in the time domain enable to differentiate between between tissue tissue characteristics and observe electrical communications within the body.

BACKGROUND OF THE INVENTION

The interactions of an electromagnetic radiation with biological tissue at different frequencies are due to different mechanisms. At low frequencies the measured conductance and permittivity are due to ionic diffusion through the cellular membrane, at middle frequencies due to polarization effects of the macromolecular membranes and at high frequencies due mainly to the water content of organic macromolecules, their polarization and relaxation mechanisms.

The dielectric constant and the conductance of body tissues have been measured as a function of a wide range of frequencies by various authors. Most of the measurements have been of tissue samples, obtained from sacrificed animals or human cadavers.

Current measurements show a factor of up to 10 times higher permittivity of malignant tumors, as compared with that of adipose tissue and only slightly higher permittivity, when compared with permittivity of muscles and glands.

The measurement method of choice has been by measuring the reflection from the open ended waveguide when terminated by the tissue sample. See (Precision Open-Ended Coaxial Probes for In Vivo and Ex Vivo Dielectric spectroscopy of Biological Tissues at Microwave Frequencies; IEEE TRANSACTIONS ON MICROWAVE THEORY AND TECHNIQUES, VOL. 53, NO. 5, May 2005). As obviously this method cannot be used for diagnosis from outside the body, several non-invasive methods have evolved.

The Dielectric constant of human tissue may also be imaged as a by-product of MRI imaging, utilizing the RF magnetic field induced by the RF coil, to reconstruct the dielectric constant and conductance distribution in real time, although this method may be an "overkill" from the cost point of view. (see http://www.ncbi.nlm.nih.gov/pmc/articles/PMC4113345/).

In principle the RF magnetic field ($B_1$) induced by the RF coil, which detects the Larmor frequency oscillates at the of the target nuclei, reorients the net nuclear magnetization of the spins so that a MR signal can be induced and detected by the receive coil. Both the excitation of the nuclear magnetization and the reception of signal intensity rely on interactions between applied RF magnetic fields and local electrical properties, namely the real dielectric constant $\varepsilon_r$ and the conductivity $\sigma$. Knowing the magnetic $B_1$ transmit and receive fields provide the necessary information for extracting the local permittivity $\varepsilon_r$ and conductivity $\sigma$. see (magnetic resonance based electrical properties Tomography—http://www.ncbi.nlm.nih.gov/pmc/articles/PMC4113345/#!po=69.53-13)

There are numerous research papers attempting to map the permittivity of body tissues by irradiating the area with microwave beams and reconstructing its permittivity from the distribution of the scattered radiation detected from the outside the area. The different implementations of the method attempt to solve the electromagnetic inverse scattering problem, which in principle is ill-posed. If an "a priori" assumption of a solution is assumed, the real solution may be arrived at by successive approximations, using for example the Newton-Raphson method. "Regularization" techniques attempting to resolve the ill-posed problem of scattering, may enable to reconstruct simple phantoms, such as a small high dielectric constant sphere depicting a tumor, within a large low dielectric constant sphere, depicting the breast. However in practical applications, where there are high permittivity contrasts between adjacent tissues, the high permittivity contrasts between adjacent tissues, trump the possibility to arrive to a unique solution and result in "smeared" reconstructed images.

Measuring the scattered radiation from a tumor in order to find its location and permittivity is strewn with measurement problems that result in very low signal-to-noise ratios. The path of an electromagnetic wave to a presumed tumor and back is twice the distance to its one-way position and in all cases leads to a very low signal-to-noise ratio. as evidenced by the poor images obtained.

Breast cancer is the most common malignant disease in women worldwide. According to the International Agency for Research on Cancer (IARC) in 2012. there were 14.1 million new breast cancer cases diagnosed and 8.2 million cancer related deaths, worldwide. The estimates show that in 2012 there were 32.6 million people alive, over the age of 15, that were diagnosed in the past with breast cancer. X-Ray mammography still remains the "GOLD standard" for diagnosing breast cancer, despite its many limitations such as 10-20% false negatives. in the USA in the 12 months, thru Sep. 1, 2015, 39,052,521 mammography procedures were reported by 14,963 full Field Digital Mammography units; namely an average of 2681 procedures/year.

Most countries recommend screening mammography every year after age 40 and every 2 years from age 50 and on (to age 69 in Europe) and to age 74 (in US). The different recommendations are a compromise between the proven benefits of early detection and the potential damage of X-ray radiation. In addition to the potential X-Ray damage, women also feel uncomfortable with breast compression that although improves diagnosis, may be painful and discourages attending the annual checkup. False positives lead to unnecessary biopsies as roughly 10% of mammograms show images with possible tumors, but less than 10% of those are diagnosed as malignancies. Most importantly, mammography misses up to 15% of actual tumors, some of which were even detectable by palpation.

All of these limitations and their associated potential for additional health risks provide ample incentive for the development of alternative modes for breast imaging.

Ultrasound may be used to complement mammography and identify the nature of large masses but cannot be used as the sole modality for breast cancer imaging.

Melanoma is the least common of skin growths, but the most deadly one. It is estimated that in the USA there will be around 75,000 new cases of invasive melanoma and around 10,000 deaths, in 2015.

The incidence rate of melanoma has doubled since 1973. Currently there is no foolproof, non-invasive test for detecting melanoma, but having a skin biopsy.

In summary, there is great importance in developing a non-ionizing diagnostic method that can differentiate between Benign and Malignant growths including small growths in the margins and reduce if not eliminate biopsies.

BRIEF SUMMARY OF THE INVENTION

The aim of the invention is to provide a new modality of 3-D imaging which is sensitive to a different set of tissue characteristics, than is "density" like Computerized Tomography (CT) or Radiology in general. We claim that "changes in velocity" of a high frequency beam traversing a tissue is more sensitive to several structural factors, that "density" only, is not.

The "velocity" of the electromagnetic (EM) waves is a fundamental notion in physics and its rate in different materials can be measured by rather simple means and technologies.

The main claim of the invention is that different tissues, benign and malignant tumors for example, may be differentiated with high certainty by the respective different "velocities" of microwaves crossing said tissues. A totally different application of Velocity Tomography is in imaging the "routes" of "action Potentials" in the body, for example in the Heart and Brain, applications that may open new eras in Cardiology and Brain science.

Using "velocity" as the parameter of choice, has practical advantages, as "velocity" defined as the "time" that takes for going from point A to point B, can be measured with extreme accuracy of up to and beyond $10.^{-13}$ of a second with modern electronics, unlike "attenuation" which is extremely more 165 complex to measure for determining "density". Consequently many biological phenomena and functions may be differentiated by their interaction with electromagnetic waves that change their speed, even when these differences are extremely small. The practical challenge is to lay down experimental setups that enable the fine and highly accurate time measurements to be the decisive factor in proving or disproving certain time-related facts irrefutably.

The greatest impact of this new imaging modality on the worldwide health scene is expected to be on early detection of malignancy, using a non-ionizing radiation, with high specificity and sensitivity, including imaging, of margins around tumors.

The practical benefits of the "Velocity Tomography" will enable early detection of Breast cancer, Prostate cancer, Melanoma, and other malignant growths, as well as allowing recurring examinations as often as required and at any age, without trying to balance examination benefits versus possible damage incurred by unnecessary ionizing radiation damage.

Table 1 below gives the "Taversing Velocities" and the "Densities" of different organs that have different tissue compositions; obviously the traversing velocities also differ within organs, at the cellular level. It is interesting to note that the "Taversing Velocities" variances between the different organs is larger than the "Density" variances between the same organs. This is a macro-indication that tissue differentiation by "Traversal Velocity" may be a better tool than using "Density" as Radiology does for more than a century.

TABLE 1

TRAVERSAL TIME/DISTANCE OF ORGANS COMPARED WITH THEIR DENSITIES at a frequency of 2 GHz

|  | (1/V) picosec/mm | Density gr/cm$^3$ |
| --- | --- | --- |
| Blood | 25.6 | 1.05 |
| Blood vessel wall | 21.8 | 1.13 |
| Bone (cancellous) | 14.5 | 1.18 |
| Brain (cerebellum) | 22.5 | 1.046 |
| Brain (Grey matter) | 23.5 | 1.045 |
| Brain (white matter) | 20.1 | 1.041 |
| Breast Fat | 7.6 | 0.911 |
| Breast Gland | 25.3 | 1.041 |
| CSF | 27.2 | 1.007 |
| Cervix | 23.2 | 1.105 |
| Dura | 21.7 | 1.174 |
| Heart muscle | 24.9 | 1.081 |
| Kidney | 24.4 | 1.066 |
| Liver | 22.0 | 1.079 |
| Lung inflated | 15.2 | 0.394 |
| Lung Deflated | 23.4 | 1.050 |
| Muscle | 24.3 | 1.090 |
| Pancreas | 25.3 | 1.087 |
| Prostate | 25.4 | 1.045 |
| Skin (dry) | 20.7 | 1.090 |
| Spleen | 24.3 | 1.089 |
| Stomach | 26.4 | 1.088 |
| Tendon | 22.0 | 1.148 |
| Testis | 25.4 | 1.082 |

Macro-tissue differentiation by "Traversal Velocity" may be a better tool than using "Density", as Radiology does for more than a century.

10 GHz microwaves at $.\epsilon._{r}\gtoreq .64$ dielectric constant tissue have a about. 1.2 mm half wavelength; features at a distance of 0.1 wavelength differences (.about.200 .mu.m) can be visually discerned. This means that microwave Velocity Tomography may complement histology, for example for imaging Giant Cells.

Thus imaging the changes of traversal velocities at the boundaries and insides of Giant cells may be indicative of related sicknesses, without resorting to biopsies.

As time intervals may be measured down to an accuracy of 100 femtoseconds, in areas as small as 100-200 .mu.m, there is a large opportunity to develop new diagnostic tools based on "Velocity Tomography as normal traversal times of tissues will definitely change when they inflate for example, due to illnesses. Consequently change of local velocity may be a Grand Indicator not only of malignancy, but also of malfunctioning organs or mechanisms in the body, like Temperature is.

Selecting the differentiating physical parameters measurable in terms of Velocity is only part of the proposed new modality; the other part, is the measurement methods that make this modality practical.

In this document we describe the tools and methods, that enable to maximize the signal-to-noise ratios (S/N) at relatively large penetration ranges of microwaves, with acceptable time resolutions.

As mentioned above we have selected "Velocity" of a "traversing" beam, as the parameter that can differentiates malignant from benign tissues, and displaying the "Velocity Image" of an organ as the medium that can convey more information than a mammogram.

The technologies described in this application help push the limits hindering medical imaging with microwaves in general; the apparent disparate requirements of "high resolution" and "high penetration" of body tissues concurrently. This topic will be dealt with, below, in conjunction with FIG. 2, in section "DETAILED DESCRIPTION OF THE PREFERRED EMBODIMENTS" below.

BRIEF DESCRIPTION OF THE DRAWINGS

FIG. 4 illustrates a mammography imager based on the velocities of the EM rays traversing the pendant breast from all around at consecutive levels thus "Velocity Imaging" the entire volume of the breast.

FIG. 7 illustrates a mobile Non-Xray microwave Tomograph for imaging small organs, soft tissues and sport injuries.

DETAILED DESCRIPTION OF THE PREFERRED EMBODIMENTS

Figure 1:
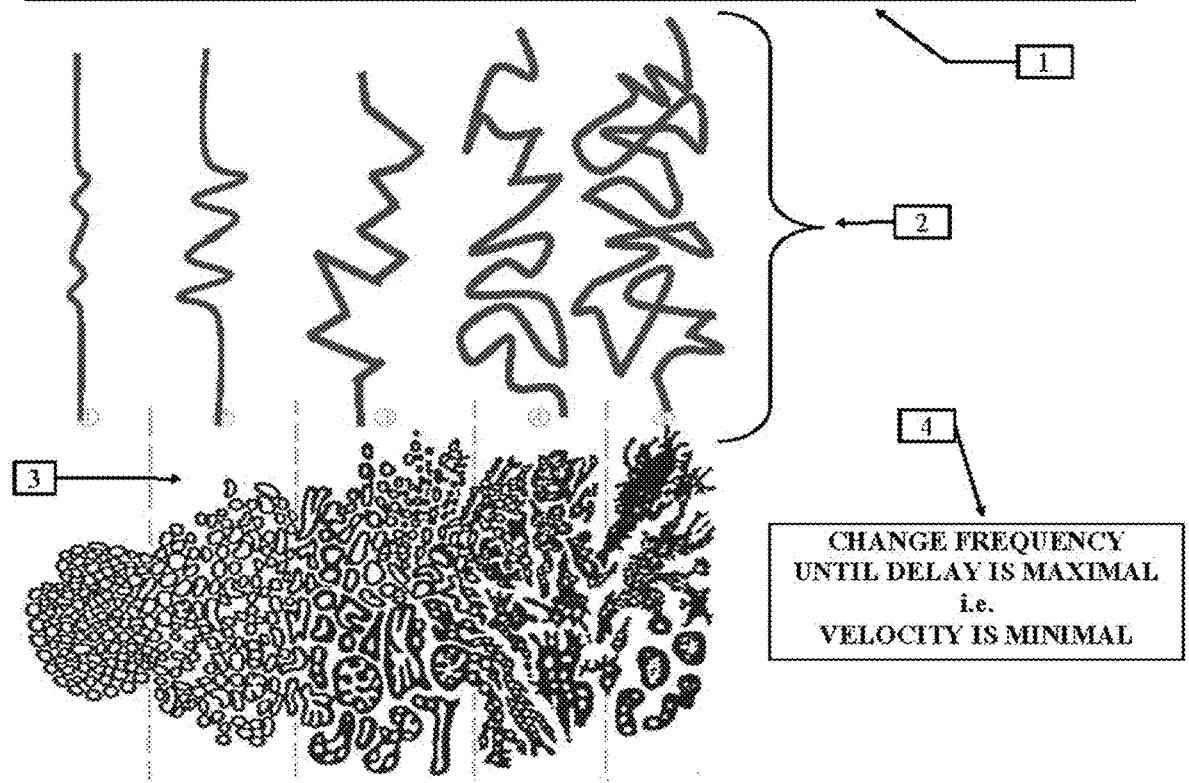
FIG. 1 illustrates the difference between benign and malignant tissue in terms of velocity of the traversing microwave beam at frequencies which are a function of the tumor size.

FIG. 1 illustrates the difference between benign and malignant tissue in terms of velocity of the traversing microwave beam at frequencies which are a function of the tumor size.

Malignant tumors may be differentiated from benign ones, by many characteristics. including "stiffness", "viscosity" and "density" which are hard to quantify unequivocally and translate to a medical device.

A benign tumor over adipose fat, is a local slow growth tissue with well defined boundaries, while a malignant tumor has an irregular shape and tends to quickly grow and metastasize invading neighboring tissue We chose 5 characteristics that cause the traversal velocities of microwaves, to be significantly lower when traversing malignant rather than benign tissues, specifically because their cumulative effect measured with high accuracy timing methods enhances the differentiation.

(1) Scattering—the internal structure of a malignant tumor which is strewn with micro ramifications scatters a traversing beam much more, than a benign tumor which is rather homogeneous.

Multiple scattering events, within the irregular tumor, caused by discontinuities between denser malignant tissue and ordinary cells, slows the traversing beam. The advance of the microwave beam with a wavelength smaller than the tumor's size, within the tumor is like the advance of the "Drunkard Walk"; its advance is proportional to the square root of the cumulative distances it crosses between scatterings. The traversal velocity of the beam, within the tumor, declines with the number of scatterings it undergoes; whether by the square root or not is, dependent on the internal structure of the tumor. However it is clear that the traversal time decreases in malignant growths that have more internal structure, than in benign growths or in ordinary adipose tissue. As this decline in traversal time increases with frequency (wavelength, decrease), scanning of the tissue ought to be optimized and done at the highest frequency compatible with the range optimal for the application. This optimization requires different devices.

Permittivity—the relative dielectric constant ($\epsilon_r$) of malignant tumors has been measured to be much higher, by as much as 40% than that of benign growths 70 vs 50; the distribution being very wide there is some overlap ($\epsilon_r$) around 55, making the classification based on ($\epsilon_r$) alone, not conclusive. However much of the data is from cadavers that do not contain blood, present in real life samples. Taking in account the angiogenesis process the distribution of the dielectric constant should be narrower and closer to 70, and the velocity which is proportional to $(\epsilon)^{-1/2}$ should be about 15% lower.

Angiogenesis—Malignant tumors are strewn with blood capillaries that, have a high relative dielectric constant ($\epsilon_r$) around 70, that slows the velocity of the traversing beam significantly when crossing the blood arteries and capillaries. while benign growths that do not need excessive blood supply will not impede the traversal time.

4. Tortuosity—Vascular and arterial Tortuosity increase the path of blood circulating in a tumor and consequently the stroma-to-blood interfaces that the microwave beam, has to cross, leading to more scattering and larger delay.

5. Polarization—Malignant tumors will strongly depolarize polarized beams in contrast with little 365 depolarization when traversing a benign tumor. Determining traversal time with a polarized beam and measuring its remaining degree of polarization at the receiver, after traversal of the tumor, in comparison with repeating the experiment with, an un-polarized beam will show the difference between malignant and benign tumors.

The differentiation between Benign and Malignant tumors in terms of the delay of the polarized microwave beam, is cumulative to the other factors mentioned above.

FIG. 1 also shows the histology (3), "GLEASON' malignancy grading patterns of 1 to 5; the 5 microwave beam paths, (2), over the GLEASON pattern, illustrate the cumulative effect of the 5 factors cited above, on the traversal path of a microwave beam traversing tissues with different grades of malignancy. Without being quantitative it is clear the traversing path becomes longer with increased malignancy.

As the interaction of the microwave beam with the internal structure of the tissue is wavelength dependent, it is clear that the optimal traversal time is found experimentally by measuring it at different wavelengths (4).

Figure 2:
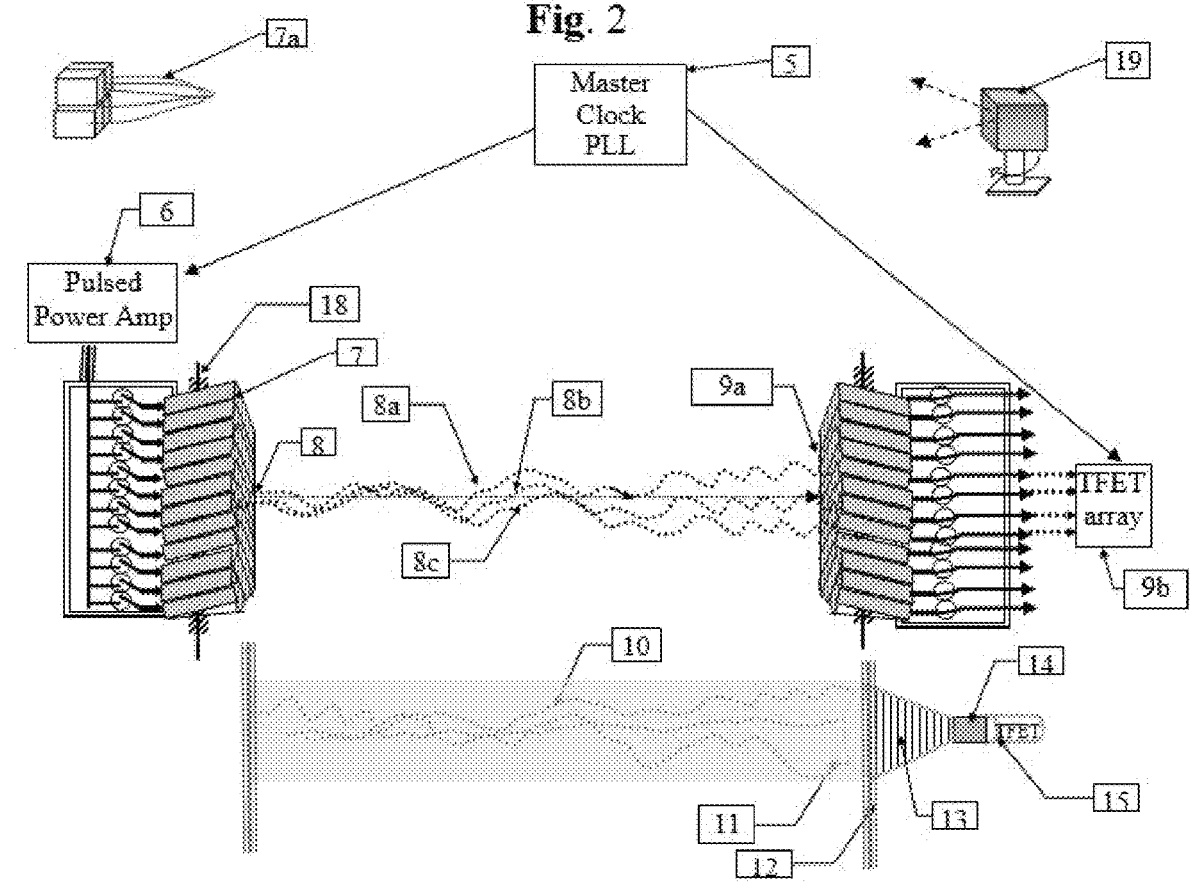
FIG. 2 illustrates the use of directional Dielectric Resonant Antennae (DRA) both as Transmitters and Receivers of polarized microwave beams to determine the FERMAT least time route.

FIG. 2 illustrates the use of directional Dielectric Resonant Antennae (DRA) both as Transmitters and Receivers of polarized microwave beams to determine the FERMAT least time route. The two great advantages of DRAs is their reduced sizes as $(\epsilon)^{1/2}$ for the same frequency as compared with regular metal antennae and higher efficiencies, exceeding 95% conversion. For example, the half wavelength ($\lambda/2$) of a Strontium Bromide crystal that, has a dielectric constant $\epsilon=300$ that emits a 5 GHz beam is $1/2[(3.10^{10})/(17)(5.10^9)]=1.7$ mm and the 90% wavelength beam which is visually discernible, is 340.mu.m. Directional arrays may be obtained by joining 4 phase-locked DRAs (7a). Several millimeter wide DRAs may be mechanically mounted on a linear piezo motor 18, at some distance apart each from the other; the linear piezo motor can advance the mounted antennas at 0.1 mm steps, for scanning a slice of the tissue with thin directional beams, "one-ray-at-a-time". As the distance to move from one position to another is as small as 1 millimeter, the time to move from one position to the next may be as little as 100 microseconds.

The need for a high, density of adjacent beams is in direct conflict with another primary design consideration: the need to minimize mutual electrical coupling between antennas. Mutual coupling between nearby antennas is the result of the current flowing in one antenna inducing current in other nearby antennas. To minimize said mutual conductance, high conductance partitions, for example made of air-graphene-air, are placed between the DRAs.

Dielectric Resonant Antennas are less prone to mutual conductance effects as their side walls are not metallic but "air" causing radiation to be reflected back. Our principle of "one-ray-at-a-time" also reduces any mutual conductance effect, if non-existent.

In practical terms, the crossing of a 10 cm non-magnetic tissue such as the Breast which is part adipose and part fibrous muscle, having an average relative permittivity of $\epsilon_r \approx 9$, for example, takes 10 $[1/(3.10^{10}/(9)^{1/2}]=10^{-9}$ seconds. Similarly the ½ wavelength of 5 GHz microwave beam in a medium with $\epsilon_{r9}$ is 1 cm; and when traversing a tumor with $\epsilon_{r\text{-}64}$ the $\lambda/2$ wavelength is 3.7 mm.

Higher resolutions require operating at higher frequencies where the attenuation is much higher.

However, in spite of larger attenuation, it is possible to reach larger distances with high frequency microwaves, by using very high amplitude, very narrow pulses, so that the deposited energy will still be very low, and therefore not damaging.

Measuring elapsed time, which can be done with extraordinary precision, across the breast is independent, of the intensity of the pulse after crossing the required distance, and requires only the triggering of the receiver. Thus a high amplitude signal will reach farther in spite of being attenuated more, and will trigger the receiver if in the end it has sufficient photons to do the job. Moreover repeating the transmission of the initial signal (n) times, will increase statistically the cumulative number of photons reaching the end of its range that will trigger the receiver. A statistical argument may be made that after (n) repetitions the range (R) will increase by ($\Delta R$) equal to $(n)^{1/2}$ times the residual photons needed to trigger the receiver, given their specific attenuation rate. Thus, what is needed is, just repeating the initial signal (n) times, until the cumulative attenuation still leaves enough photons "alive" able to trigger the receiver. This can be achieved by suitable coating of the walls of the receiver that prevent absorption. As traversing an organ at microwave frequencies, takes only a few nanoseconds, repeating the exercise, say $(n)=10^2$ times, takes only several microseconds. This process is equivalent to increasing the intensity (n) times with the difference that the total energy is dissipated during a longer interval of time cumulatively. This increase of traversal range also enables to work at higher frequencies that enable higher resolutions. Repeating the signal (n) times also improves the accuracy of the "elapsed traversal time".$\Delta t$, which is essential to our method.

Figure 2A:
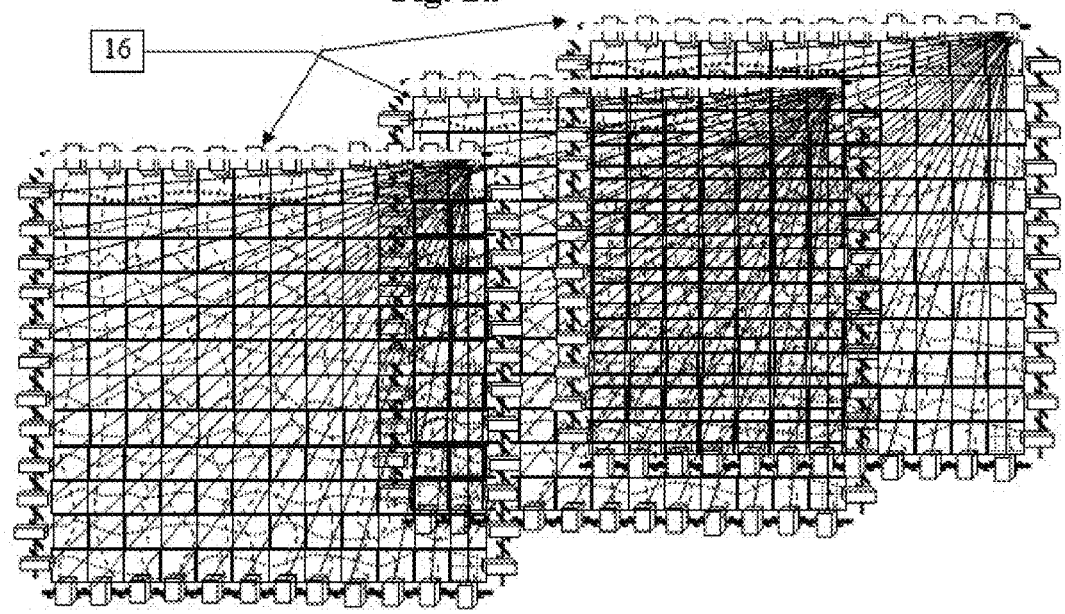
FIG. 2a illustrates the reconstruction of Velocity tomography with arrays of Fermat-Rays and the process of determining the velocities of segments of the route of a microwave beam on its route from the transmitter to the receiver.

FIG. 2a describes the process guiding the selection of "velocity rays" from multiple directions, in order to be able to map slices of the breast. We require generating "one-ray-at-a time" in order not to confuse the receivers with scattered remains of previous pulses.

As elapsed time across a ray is extremely precise and the duration (t) of 1 mm segment of a 10 cm ray in tissue with average permittivity of $\epsilon_r=16$ being $t=s/v=(0.01)/(4/3.10^8)=13.10^{-12}$ seconds, the needed velocity accuracy of a 1 mm path will be of the order of femtoseconds which is attainable with advanced electronics.

The display of the Velocity tomography is similar to that of radiology, only without X-rays: the range of 1 picosecond/mm to 1 nanosecond/mm is color coded, from white to black, to display a 1000 to 1 range of differential velocity (or its reciprocate, slowness).

Differentiation of tissues such as benign and malignant tumors in breast cancer, skin melanomas and dynamic imaging of "stroke", and "carotid" are possible applications with the above described technology.

In Velocity Tomography, optimal imaging is a function of the wavelength and the length of the traversal path; as the sizes of the suspected growth(s) are unknown a priori, after the initial image, the physician may decide to repeat the imaging at a different microwave frequency and/or concentrate at a specific slice that offers better contrast.

One major advantage of the above described Microwave breast cancer detection, is that the examination may be repeated at short intervals of time, if suspicions arise as to the nature of a suspected growth or the, mode of imaging. One doesn't have to wait, certainly not, for a year, to follow the evolution of a suspected growth. The examination may be repeated any time using the different options offered by the system.

Figure 5:
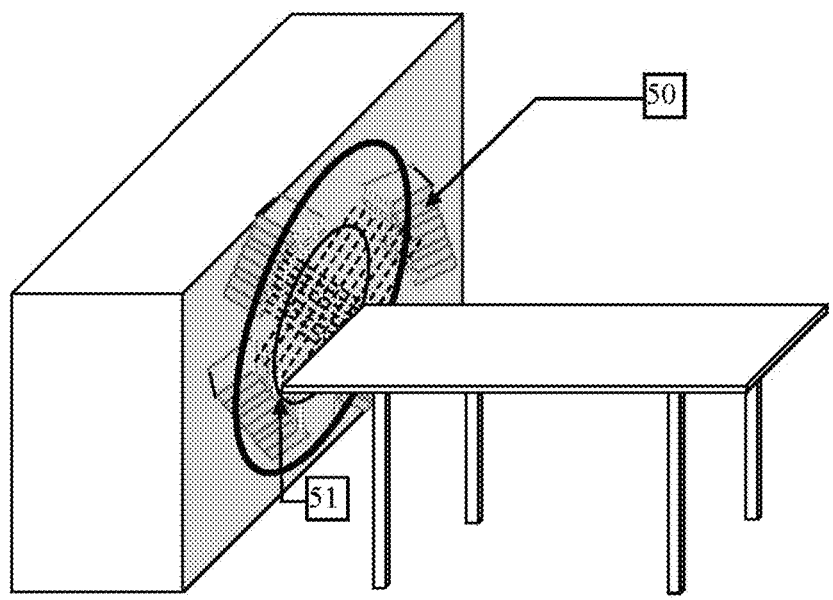
FIG. 5 illustrates a non-XRay Microwave Tomograph tuned specially for imaging, soft tissues, children and newborns.
Figure 14:
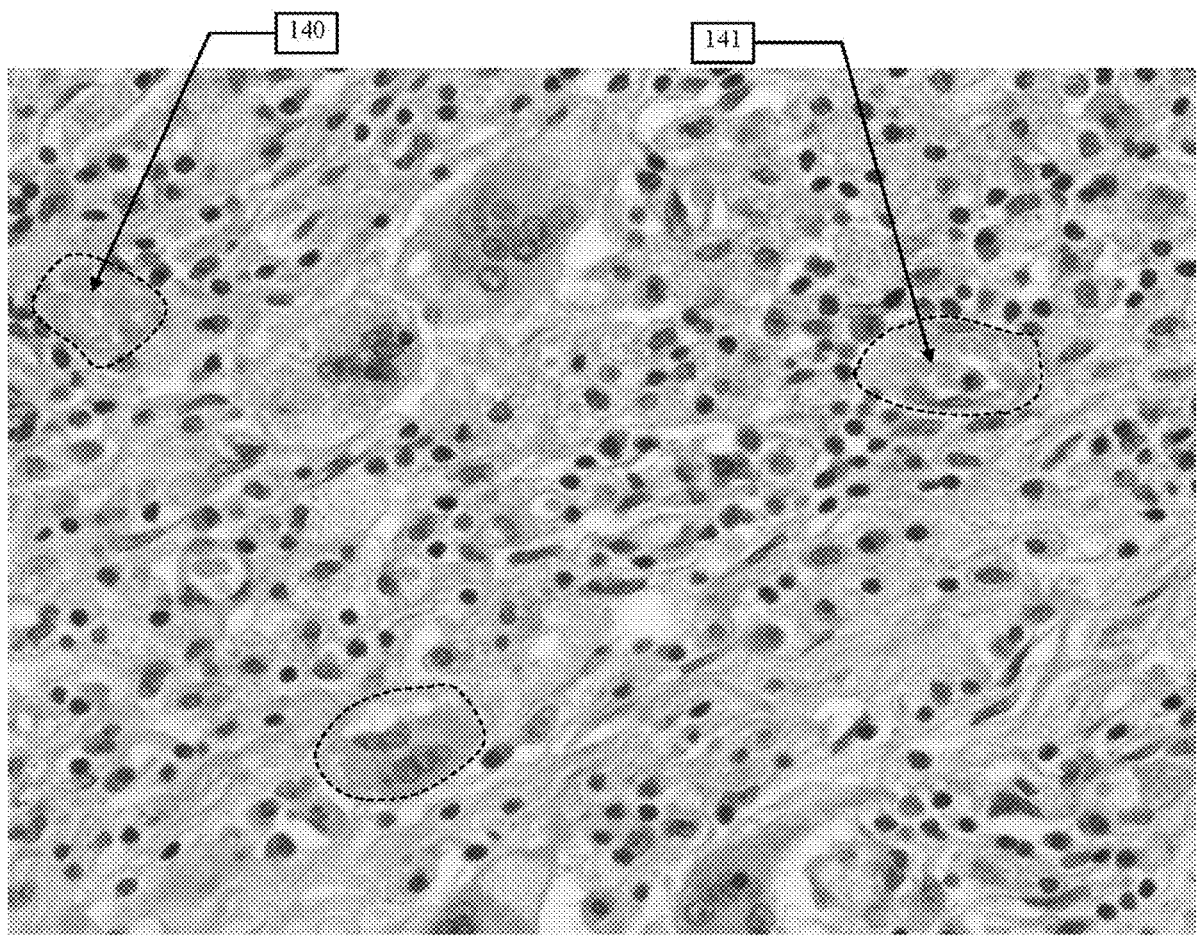
FIG. 14 illustrates the velocity imaging of a tissue slice containing Giant Cells in order to determine its malignancy.

Dynamic imaging of the advances of polarization traces, at 10 to 1000 frames/sec, on smaller regions of the brain or the heart, as described in conjunction with FIGS. 5 and 14 may be followed, enabling to trace electrical communications across the brain or the Heart muscle.

Both the transmitter and receiver DR antennas 14 are coupled to narrow collimators 11 that restrain the aperture of the emitted and received beam 10. However there is a need to couple the beam emitted or received by the antennas 14 that have a specific dielectric constant to that of the medium 10 (the pouch that holds the breast) which the beam will traverse. In order to minimize reflections, the inside 13 of the collimator and the material 12 that, holds the medium in which the beam propagates, have to be of materials that gradually change and match the dielectric constants of the materials at their ends.

The receiver antenna 14 is coaxially coupled to a Tunneling Field Effect Transistor (TFET) that needs only a minimal number of photo-electrons to trigger the following electronics. FIG. 2 also illustrates the measurement of the velocity along an EM ray between a transmitter and a receiver when traversing a tissue. The figure illustrates the different paths, 8a, 8b and 8c taken by an EM wave transmitted by one antenna 8. In the absence of a Receiver array 9a, the electromagnetic wave will advance in all directions until it dissipates. However in the case that there are receiver antennas in the general direction of the EM wave, the path that the wave will take is, according to the Fermat "least time" principles the path that can be traversed in the least time. This is a powerful tool that enables to analyze the propagation of electromagnetic waves in terms of "rays". Velocity in terms of "ray" paths completed in "least time" enables to simplify tomography of electromagnetic waves, by treating them as "least-time-rays" in the time domain, one-ray-at-a time, and avoiding analysis of wave interactions, possible reflections and refractions. Consequently a complete set of independent "rays", enables Reconstruction of a "velocity map".

Different paths between a transmitter and a receiver may differ by small amounts in the time domain, reflecting the wave nature of the beam; consequently it is the precision of the traversing duration that also determines the "width" of a ray, and consequently the spatial resolution of the final image. To this end, the "start" and "end" of crossing a distance are measured with high accuracy using Phase Locked Loop technology with precision absolute clocks. This meticulous selection of the rays traversing the tissue, "one-ray-at-a-time" after ensuring that "all is quiet" eliminates remaining clutter from previous rays and determines the high spatial, resolution of the interaction with the tissue, beyond its high frequency.

We require generating "one-ray-at-a time" in order to avoid triggering the receivers with scattered remains of previous pulses. "Stacking" the traversal measurements multiple times increases the range of the EM beam. Repeating the transmission of the initial signal (n) times, will increase statistically the cumulative number of photons reaching the end of its range. Consequently after (n) repetitions, there will be at the end of the range of the signal, sufficient number of photons that will trigger the receiver.

Statistically after (n) repetitions the range (R) will increase by (.DELTA.R) equal to $(n)^{1/2}$ times the residual photons needed to trigger the receiver, given their specific attenuation rate. Thus, what is needed is, just repeating the initial signal (n) times, until the cumulative attenuation still leaves a level able to trigger the receiver. As one traversal measurement takes a few nanoseconds, repeating the process $10^2$ times for example, will still take several microseconds which improves signal/noise ratio by a factor 10 and extends the range.

Imaging a section (10 cm.times.10 cm) of the body with 1 mm accuracy requires $10^4$ longitudinal rays. At 1 GHz frequency and average dielectric constant $\epsilon_r=9$, the velocity of the microwave beam being $10^9$ cm/sec repeating $10^2$ times, an attempt to cross a certain distance is like increasing the intensity of the beam by 10 as random noise increases only by the square root of $10^2$.

As photons at the end of their course do not immediately die, and if the receiver wails are preponderantly reflective (air for example, as it is in a DRA receiver) and not absorbing, the photons will keep wandering between the receiver walls for some time. Consequently after (n=100) repetitions of the pulse, there will be at the end of the range of the signal, 10 times more signal photons that may trigger the receiver. Thus, what is needed is, just repeating the initial signal (n) times, until the cumulative attenuation still leaves a level able to trigger the receiver.

Time intervals may be measured with picosecond accuracy with modern electronics, meaning the path length of 10 cm may be measured with 0.1 mm accuracy. Sub-wavelength differential time measurements may be done by phase-locked-loop (PLL) measurements to a hundredth fraction of a wavelength.

In order to avoid any interference between physically adjacent rays, they are generated by separate antennas, sequentially in the time domain, after the previous ray has been detected, and any scatterings have died down. For example 100 parallel rays one millimeter apart, may be generated by 10 antennas 7, placed every 1 cm along a piezoelectric rail 18 that moves the antennas along the 1 cm distance within 20 milliseconds. Consequently this parallel operation will scan a 100.times.100 array also in 20 msec or less, using 50 piezo motors when the idle time between two rays that travel the 10 cm path between transmitters and receivers is at least 1000:1. Consecutive slices may be scanned consecutively with the same 50 piezo-motors, lowering them one at a time to consecutive slices, thus scanning the entire volume of the pendant breast. Alternatively and at a higher cost, each "slice" may be scanned by 400 antennas operating as transmitters and/or receivers alternatively, while each antenna is mounted on a 515 piezo-rotator that rotates an antenna up to 90.degree. within a millisecond. This geometry enables "dynamic imaging" of the same "slice" at higher frame rates. For alternative Volume scanning regime see the text associated with FIG. 5.

Figure 3:
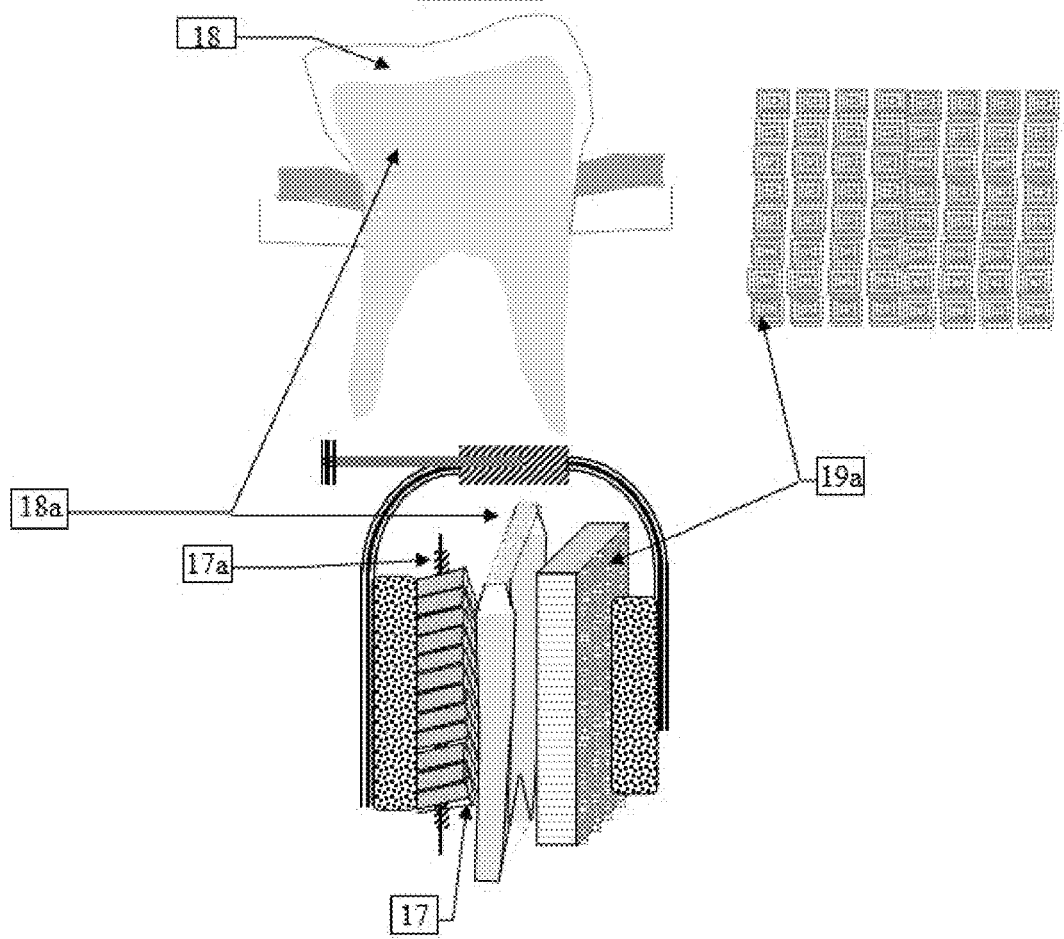
FIG. 3 illustrates the Velocity imaging of "teeth" using an array of microwave transmitters on the front and an array of microcoils that serve as receivers on the back of the tooth to measure traversal times across the tooth, which is more sensitive than the X-ray attenuation.

FIG. 3 illustrates the Velocity imaging of a tooth 18, using an array of microwave transmitters 17 described above in conjunction with FIG. 2. The linear array of DR antennas are mounted on a linear piezo-electric drive 17a that causes the array to scan the front surface of the tooth.

An array of microcoils 19a as described below in conjunction with FIG. 9, serve as receivers, on the back of the tooth, and measures the traversal times across the tooth. The distance between the antenna array 17 and the micro-coil array 19a, is calibrated continuously, by measuring the time elapsed between the corner DR antennas in the DR array and corresponding micro-coils at the micro-coil array and calibrating all the distances between Transmitter antennas and the micro-coils accordingly.

Obviously a multiplicity of such "Transmitter array+ Microcoil Receivers" can be put side-by-side for imaging several teeth at a time.

Figure 3A:
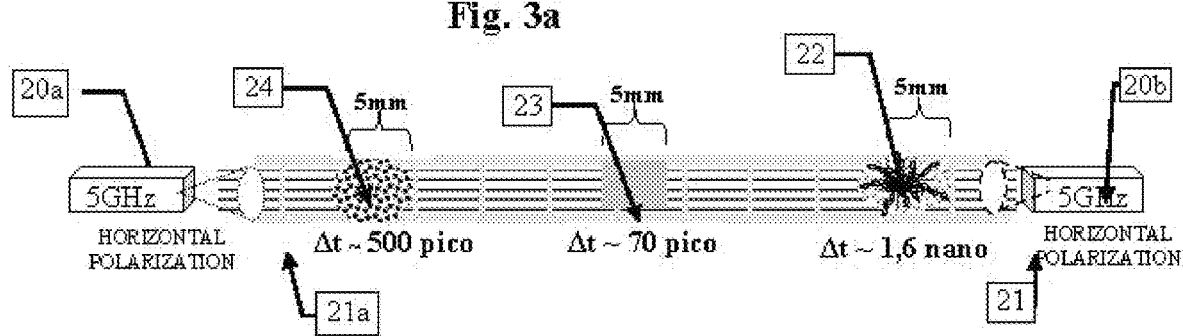
FIG. 3a illustrates the time delays incurred by a 5 GHz microwave beam when traversing normal, benign and malignant tissues.

FIG. 3a illustrates the calculated approximate traversal times of 5 mm wide of adipose, benign and malignant tissues by 5 GHz frequency, collimated beam of 2 mm diameter opening. The effects of all 5 factors namely, tissue permittivity, angiogenesis, tortuosity, scattering and depolarization on the traversal time were considered to be cumulative. The tissue permittivity which is an expression of the electrical charge stored in the tissue is related to the square root of inverse velocity, as are the vessels and arteries that populate the stroma; the tortuosity prevalent in the malignant tissue that may increase the vascular length by up to 30% increases both the blood volume that circulates in the tissue and also contributes to the scattering cross section that is proportional to the stroma/tissue ratio which also determines the ratio of depolarization. The quantification of these factors in FIG. 3a is for illustrating the order of magnitude differences between different tissues. It is important to emphasize, though, that the greatest contributor to the tissue differentiation is the forward scattering ratio that is proportional to the stroma/tissue ratio and not the charge stored in the specific tissue (dielectric constant).

Figure 3B:
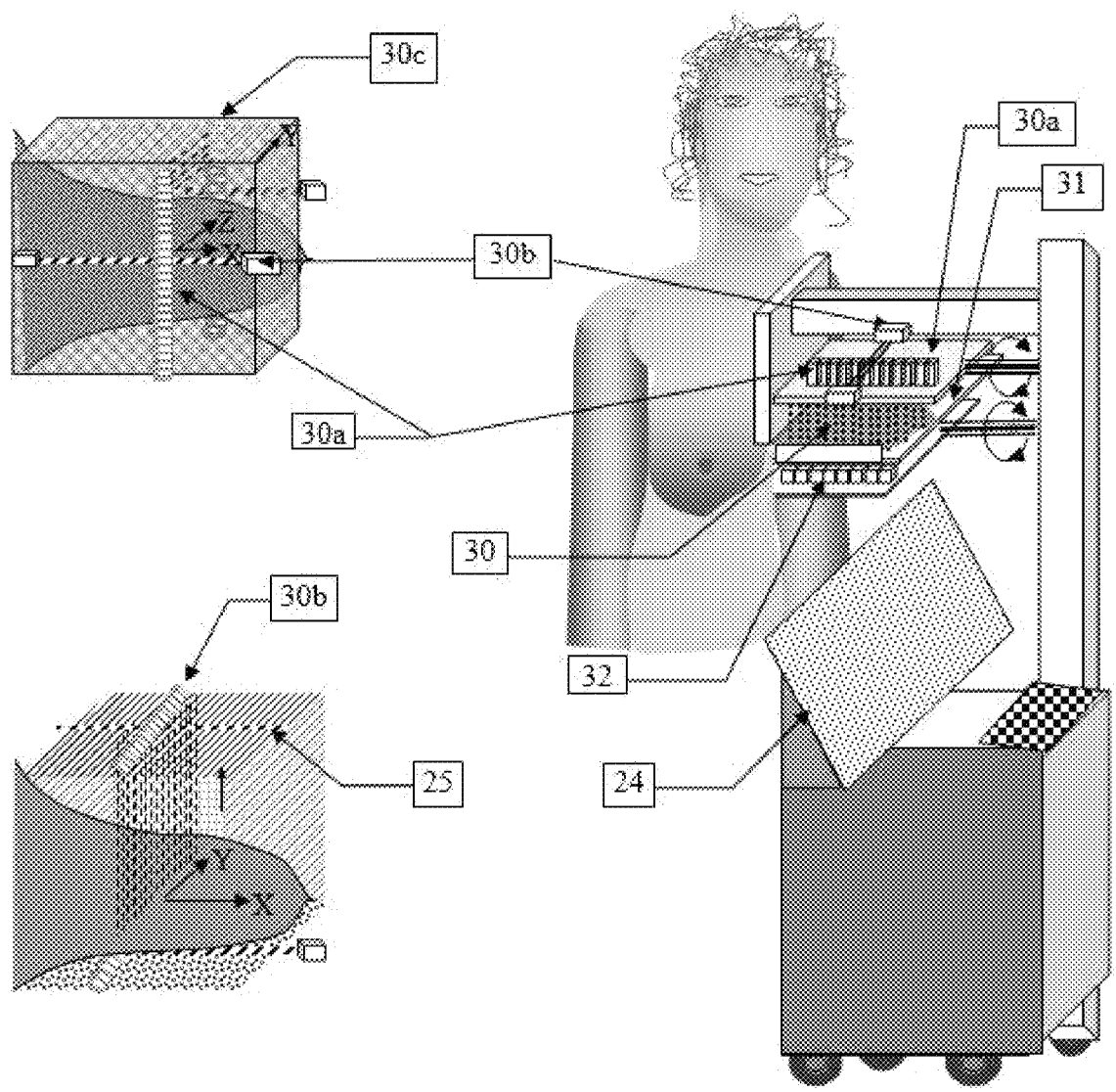
FIG. 3b illustrates a Non-X Ray mammography imager based on the velocities of the EM rays traversing the Breast from 2 perpendicular directions.

FIGS. 3b and 4 illustrate 2 modes of mammography imaging based on the velocities of the microwave beams traversing the breast.

In the simplest mode equivalent to the original classical mammography. microwave "rays" 30 generated by transmitter antennas 30a, traverse a flat non-compressed breast laying, on a thin semi-transparent plate 31; and the rays 30 traversing the breast are detected by receiver antennas 30a laying immediately behind the thin plate 31. Both the line of transmitters 30a and the line of receivers 32 move laterally on piezo motors along the length of the breast for scanning the entire breast.

The rays traversing the breast and detected by the receivers 32 form a 2D image of the cumulative traversal times across the breast.

The lateral traversal time across the breast may also be measured while the breast is still laying on the plate 31 by turning the transmitter 30a and receiver 32 arrays by 90.degree.. As the breast laying on a plate 53a is not compressed, the process of turning the transmitter 30a and receiver 32 arrays by 90.degree. may move it and/or change the positions of its internal coordinates that we wish to map in "slowness" terms, due to the breast's "smoothness" and "viscosity". To this end the breast laying on a plate is nonetheless restrained in the lateral position by two plates that restrain movement sideways. Taking a lateral velocity map of the breast will provide a view perpendicular to that previously obtained when the microwave "rays" traversed the breast in the perpendicular "Z" direction. Processing this perpendicular view as above will give the "slowness" difference from the average "slowness" in the perpendicular direction. The average of the two slowness difference values from the two perpendicular directions is a better approximation than the values obtained from scanning from one direction only.

There are several ways to display the information embedded in this image of the cumulative traversal times; as .SIGMA..sub.it.sub.i=.SIGMA..sub.i(d.sub.i/v.sub.i) and if we define a new parameter, (s) called "slowness" s=(1/v), then by definition T=.SIGMA..sub.it.sub.i=.SIGMA..sub.i (d.sub.is.sub.i)=D.SIGMA..sub.is.-i. For a given distance D traversed by the microwave beam, the cumulative time T is proportional to the cumulative "slownesses" along all the pixels; each pixel shows the cumulative value of the inverse of the velocity, along the path that traversed the breast.

If we subtract from all the pixels the average of all the "slownesses" [(s.sub.i)-(1/n).SIGMA..sub.is.sub.i] along the "ray", the new image would represent the deviations from the average "slownesses".

Thus if we translate this image into a black and white scale and assign "white" to the "lowest excess slowness=highest excess velocity" and "black" to the "highest excess slowness=lowest excess velocity", the different gradations of white will show normal tissue while the different gradations of black will show the differentiation between muscle, gland, benign and malignant tumors. Obviously the process of subtracting the average from the total, makes the gradations non-linear and dependent on the total data considered.

FIG. 4 illustrates a method for reconstructing the volume of a pendant breast in terms of velocity of EM beams traversing consecutive slices each from multiple directions using arrays of transceivers 42 mounted on the periphery of a pouch 45 holding the pendant breast Tomography in general is a set of mathematical methods that come to obtain the magnitude distribution in a volume (M.sub.x, M.sub.y, M.sub.z) of a substance D, out of the magnitudes of their projections in the 3 dimensions (x), (y) and (z). Often, finding the magnitude distribution in a plane (M.sub.x, M.sub.y) of the substance D, out of the magnitudes of its projections in 2 dimensions (x), and (y) and then stacking the consecutive planes M.sub.xy one on top of the other along the Z direction, enables to find the 3D distribution of the substance, in this case the "slowness" in voxels of the breast.

Using the projections of the magnitudes M.sub.x(t) of a linear distribution along a "Ray", will enable to determine the magnitudes M.sub.x(t) constituting the "Ray". Consequently, the magnitude distribution in a volume (M.sub.x, M.sub.y, M.sub.z) of a substance D, may be determined by adding the distributions along the "Rays" constituting the Volume, which is self evident. However, the practical value of this proposition is that, the magnitude distribution in space may also be determined when some Rays constituting the Volume may be missing, or are impossible to measure and can be interpolated from nearby measurements, in the time domain.

Tomography may be based on ray tracing, when the wavelength is small compared to the path length, by viewing the paths of electromagnetic waves as straight lines in uniform media and introducing a change of direction of the straight line as required by the Fermat, principle, when the uniformity of said medium changes. Each ray along the "Fermat" route is the sum of segments along the route, said segments changing direction as the velocity along the route changes due to changing dielectric constants.

As the length (d) of each, segment (i) equals the measured time (i) multiplied by the velocity of the EM beam in the specific segment, d.sub.i=t.sub.is.sub.1 where s.sub.i-(1/V) and in a 2D "slice" each segment d.sub.ij=t.sub.ij s.sub.ji or in matrix notation (D)=(T)(S): As all d.sub.ij elements are measurable and the square matrix (T) may be inverted, multiplying both sides of the matrix equation by the inverted matrix $(T)^{-1}$, we obtain $(T)^{-1}(D)=(T)^{-1}(T)(S)=(S)$ meaning that the slownesses $s_{ji}$ of the (d) segments may be calculated.

However in some geometries the matrix (T) may not be square, as some paths $d_{ijt.sub.ijs.sub.ji}$ may not be accessible as is the case in many medical problems.

In such cases an approximation may be used, for example by defining the missing elements as an average of nearby elements or an extrapolated continuation of nearby elements The reconstruction algorithm used in this application is the "Randomized Kaczmarz" algorithm that converges much faster than the regular Kaczmarz, the Radon or the "filtered back-projection" 610 reconstruction algorithms, by processing the rows of equations randomly, in order of their "relevance" rather than sequentially. (see "A randomized Kaczmarz algorithm with exponential convergence" by Thomas Stranger and Roman Vershynin strohmer@math.ucdavis.edu and vershynin@math.ucdavis.edu.

In our case the distribution of "slownesses" obtained by scanning from 2 mutually perpendicular directions and subtracting the average "slowness" may be used as the first iteration of the reconstruction of the breast "slices" from the "rays" crossing each "slice" of the breast, from all the 360.degree.. Combining the stack of slices, will give the slowness "map" of the entire breast volume.

FIG. 5 illustrates a "Velocity Tomograph" where an array of microwave transmitters 50 generate a parallel cluster of rays that traverse the head of a young patient and is detected by an array of microwave receivers 51. The practical problems to overcome in microwave tomography are, as explained above, attenuation of the beam and the resolutions attainable. The solutions of these problems for breast cancer imaging are applicable to head tomography too, provided that the organ to be imaged doesn't present higher attenuation and doesn't require higher resolution. For example tomography of the head of small children, taking in account the "data stacking" of hundred times and following the "one-ray at-a-time" rule, enables imaging that doesn't require very high geometrical resolution, hut rather high temporal resolutions, where microwave imaging is more suitable than X-ray tomography. Defining a "ray" as only the shortest route between a transmitter and a receiver thus eliminating all other rays, enables use of the algebraic reconstruction algorithms, as mentioned above.

The advantage of the Velocity Tomography, apart from being Non-Radiative, is its sub-millisecond Imaging speed which is orders of magnitude faster than CT and MRI, consequently making it ideal for Dynamic Imaging of body processes that change at sub-second ranges. Its Velocity range of up to 1000:1 is particularly useful for imaging continuous and fine movements of limbs while its strong attenuation, while being an impediment for imaging large organs, is particularly suitable for imaging soft and small organs such as the kidneys and dynamic imaging of their functioning. Velocity Tomography being a Non-Radiative modality is also particularly suitable for "Dynamic Imaging" of the "unborn", the "new-borns" and small children.

Figure 6:
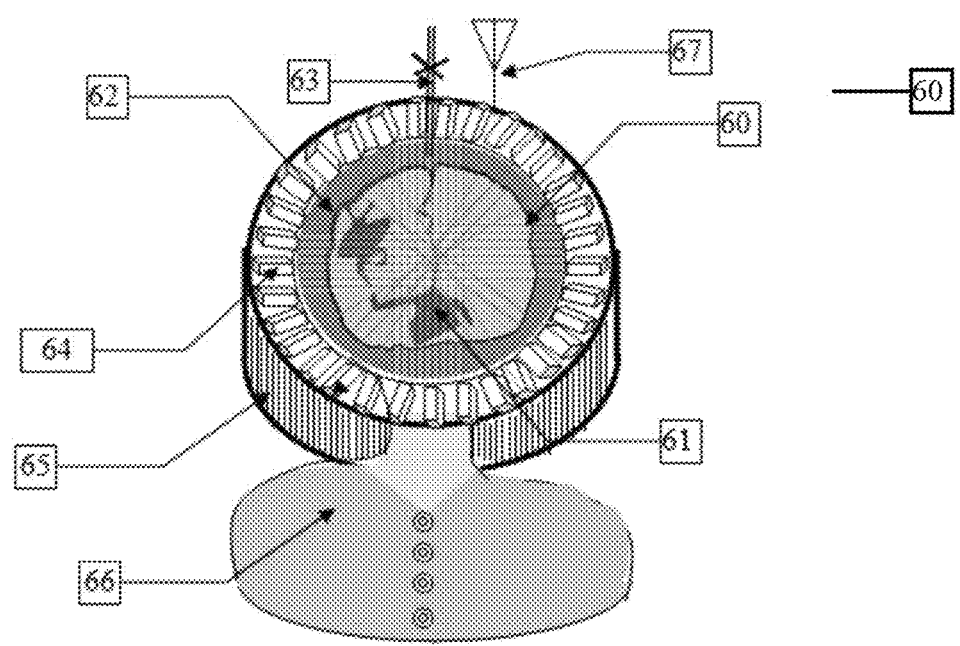
FIG. 6 illustrates a specialized hemorragic stroke detector.

FIG. 6 illustrates a helmet 65 for diagnosing an Hemorrhagic "stroke" of a patient 66. The helmet houses a circular array of microwave transmitters/receivers 64, situated around a pouch of fluid 62 that separates the user's head 60 from the transmitters 64. The pouch of fluid has an intermediate dielectric constant, between that of the skull on one side and that of the antennas 64 on the other side.

The pouch, is elastic and expands appropriately when filled thru an external pipe 63, so that it fills the space between the skull and the transmitters, snugly. The transmittal elapsed time, detected by the receivers is transmitted by wireless to an outside processor that reconstructs the velocity image of the "slice" traversed by the microwave beams. As the goal of the examination is to detect the presence of blood and its expansion maximal spatial resolution is not required and the examination may be carried out with 1 GHz microwaves and with minimal number of transmit-receive antennas. To make the design reliable and simple to operate, several circular arrays of transceivers may be included in the helmet enabling to image a number of "slices" consecutively.

FIG. 7 illustrates a mobile imager incorporating Electromagnetic transmitters 70a and receivers 70b for imaging small "organs" and soft tissue injuries such as broken bones in terms of microwave velocity. Velocity Tomography can become a highly beneficial complementary medical imaging modality in view of the significant differences in permittivity between soft/hard tissues, bodily fluids such as cysts, blood arid CSF, using non-ionizing radiation to provide quantitative images that complement classical Radiology. Bone Images based on velocity of the transmitted microwaves give a complementary image to that provided by CT as two bones having the same density may show different transmission velocities, for example if they have different internal mini-bruises that slow the transmission of the microwave beam. Velocity imaging may be carried out with a parallel array of transmitters 70a irradiating a limb and an array of receivers 70b detecting the transmitted microwaves. a Transceiver Plates 70a and 70b, enables to use different Plates of optimal dimensions suitable for specific imaging applications. The Plates mounted, on tubular supports 73a and 74a, also of different lengths, enable to adapt the Mobile Tomograph to a plethora of applications in the Hospital. As both the Transceiver Plates and the various supports may be stored within the Mobile casing the Mobile Tomograph is also transportable to locations outside the Hospital.

Figure 8:
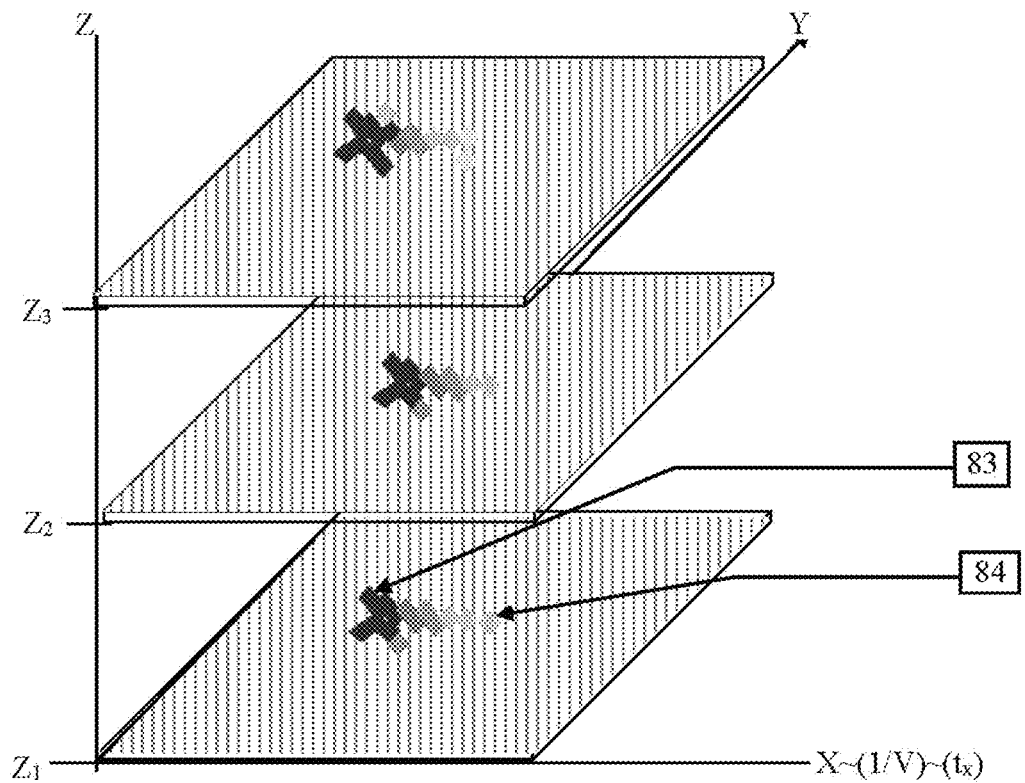
FIG. 8 illustrates the imaging of tumor margins using velocity tomography of several consecutive "slices".

FIG. 8 shows several consecutive reconstructed tissue "velocity slices" showing "malignant" tissue pixels, where the traversal velocity is very low and shown as high intensity pixels. The dynamic range of malignancy in the display is 1000:1 and all 3 consecutive slices show a trail of pixels with declining malignancy. This display of declining malignant pixels shows the, margin of cells that although less malignant have either to be excised or watched at some future date to follow their development. As their place in consecutive slices is digitally recorded and as Microwave Velocity Imaging is non-ionizing, there is no reason not to excise the partly malignant tissue and schedule another examination session, until no further malignant tissue cells are observed.

Figure 9:
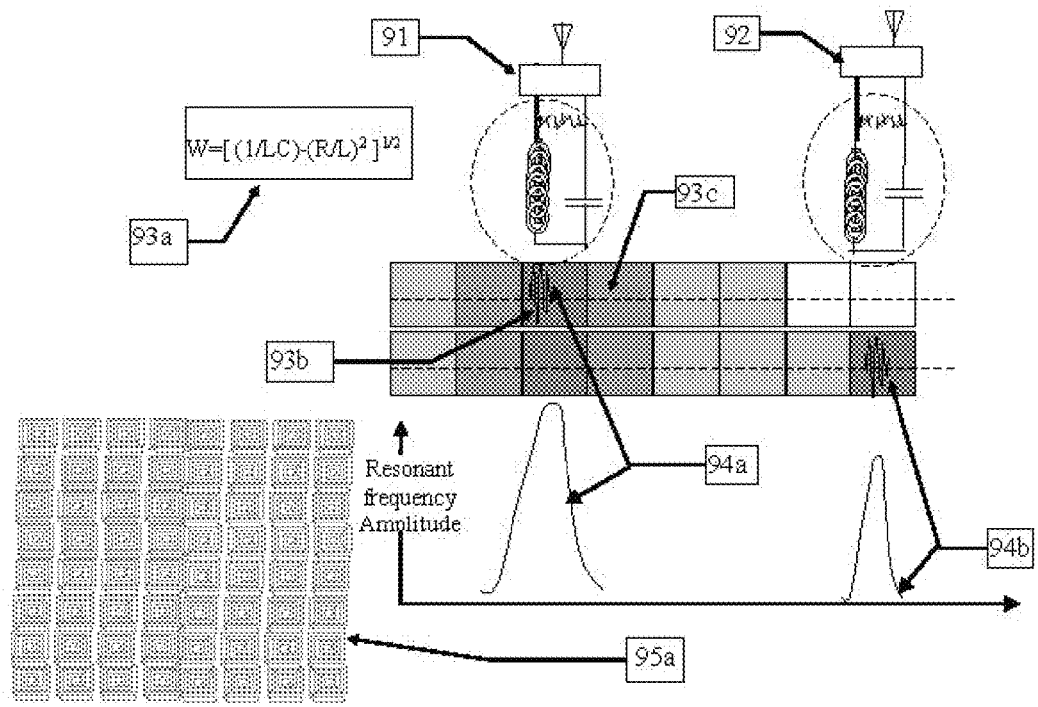
FIG. 9 illustrates arrays of ultra-high sensitivity graphene LC coils tuned to the frequency of the microwaves traversing the tissue underneath for determining the traversing time with high accuracy and consequently determining the linear traversal velocity.

FIG. 9 illustrates the use of resonant micro-LC coils as sensors that detect the time EM pulses traverse the tissue under the sensor. A CuO/graphene nanocomposite wire-wound inductor placed transversally over conducting tissue 41 will pick up the circular magnetic loop surrounding the current pulse; thus the microwave wavelet passing under the very low conductance wire wound coil will induce a current in the inductor. The lower the resistance of the graphene pick-up coil, the higher the pickup current flowing into the wires of the inductor, will be. The microwave pulse passing under the wire-wound coil moves at a certain speed V determined by the local body tissue permittivity and the original pulse frequency. If the capacitance C of the parallel capacitor connected to the wire-wound inductor in parallel is such the LC equals the frequency of the picked-up signal dI/dt, then, the picked up signal's intensity will be maximal.

Consequently the LC circuit should have a tunable capacitor 42 that can be fine-tuned until the picked up signal is maximized. Notwithstanding the fine-tuning process the LC circuit should have the minimal resistance and even cooled to reduce its resistance. The penetration of the signal depending on the depth of the path, and the original amplitude of the signal, the detected signals' strength will decrease exponentially with depth and the place along the path. LC sensors placed continuously on the body tissue along a "Ray", 93c, will signal when the traversing pulse passes underneath it, together with the exact mean time of traversal. When placed at equal intervals it will be able to monitor the changes of velocity from one segment of the path to another.

The system is of great value for detecting malignant tissue on the skin surface and near the skin surface. Averaging the picked-up signals of neighboring pick-up coils increases the average position of the electrical pulse passing under the coil.

Figure 9B:
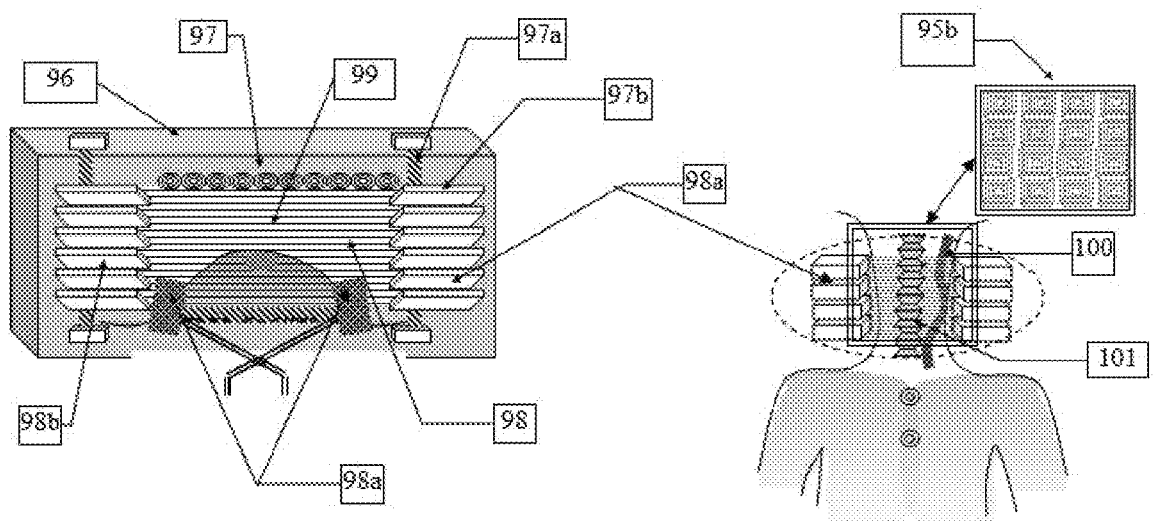
FIG. 9b illustrates 2 applications of the "Linear Velocity Tomograph" using linear coil arrays, suitable to measure velocities of microwave beams propagating close to the surface of the body for determining malignancy of a melanoma and the imaging of neck injuries and carotid artery imaging.

FIG. 9b illustrates a relatively small "Linear Velocity Tomograph" 96 that has an open window 98 that allows to position the organ to be imaged, between two arrays of antennas 98a, 98b that can operate both as transmitters and receivers alternately. The antennas sit on rails 97a and can move up and down as needed. Each of the antenna boxes 97b contains several parallel DR antennas that can be operated separately or in tandem.

Immediately above the antenna boxes are an array of LC coils 97 that sense the passage of a microwave wavelet underneath and report its passage and time. The antennas used are described above in conjunction with, FIG. 9. Here, as in all microwave arrays of this invention, the "one-ray-at-a-time" rule is observed. Accordingly, the velocity of the ray traversing the organ is determined by the timings initiated by the triggering of the LC coils, while the position is determined by the array of antennas.

The classification of skin tumors in terms of a microwave pulse's traversing velocity, is probably the most useful innovation of the "Linear Velocity Tomograph" that will impact healthcare. Once the traversing velocities for the various growths from benign to malignant, are established, the identification of all the skin growths may be routine. FIG. 9b illustrates, the positioning of the mini "velocity-imager" on a melanoma tumor protruding on top of the skin after being squeezed laterally with a forceps like tool 98a.

Skin Growths may be examined by first "squeezing" them at their periphery, to make them protrude out of the skin surrounding the growth, and then introducing them onto a "Linear Tomograph" where the linear Velocity along a Ray from the Transmitter to the Receiver, is measured by an array of "inductive coils" viewing the passing Rays from atop. Following the principle of "one-ray-at-a-time", the velocities of all the rays traversing, the growth are measured sequentially, enabling to obtain the local traversal Velocity as limited by the local coils viewing the traversing beam from above.

Figure 10:
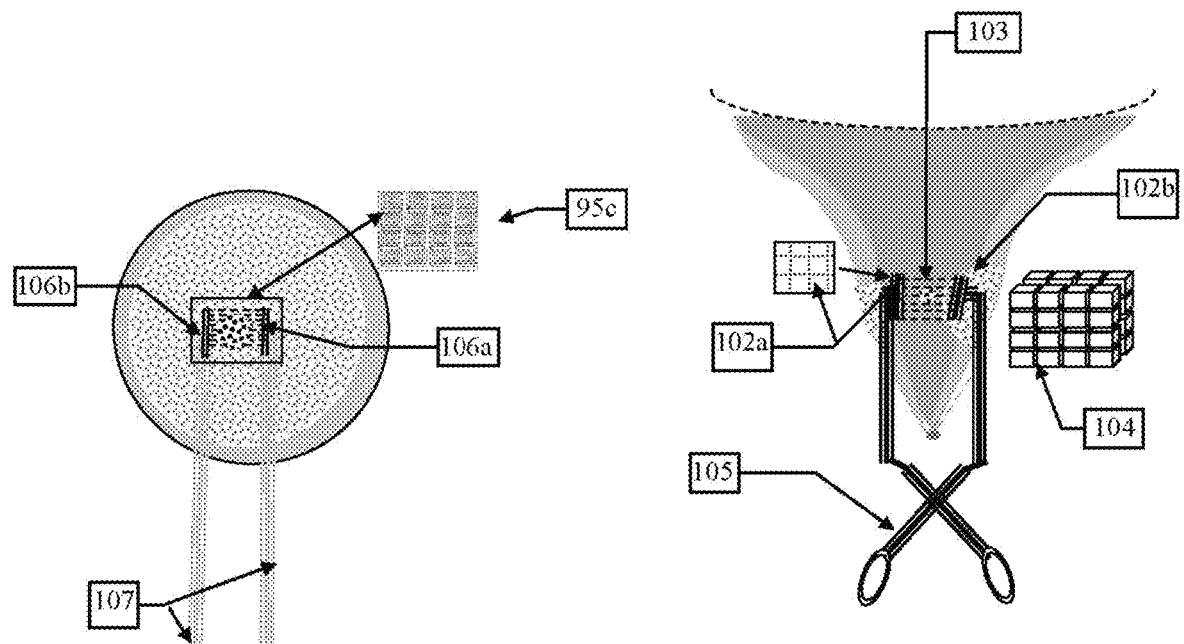
FIG. 10 illustrates 2 devices for measuring the traversal velocity of an electromagnetic beam, of a suspected lesion within the breast, one in vivo within the breast using a double needle syringe and the second by measuring the traversal time of a squeezed part of a protruding part of the base of a pendant breast.
Figure 10A:
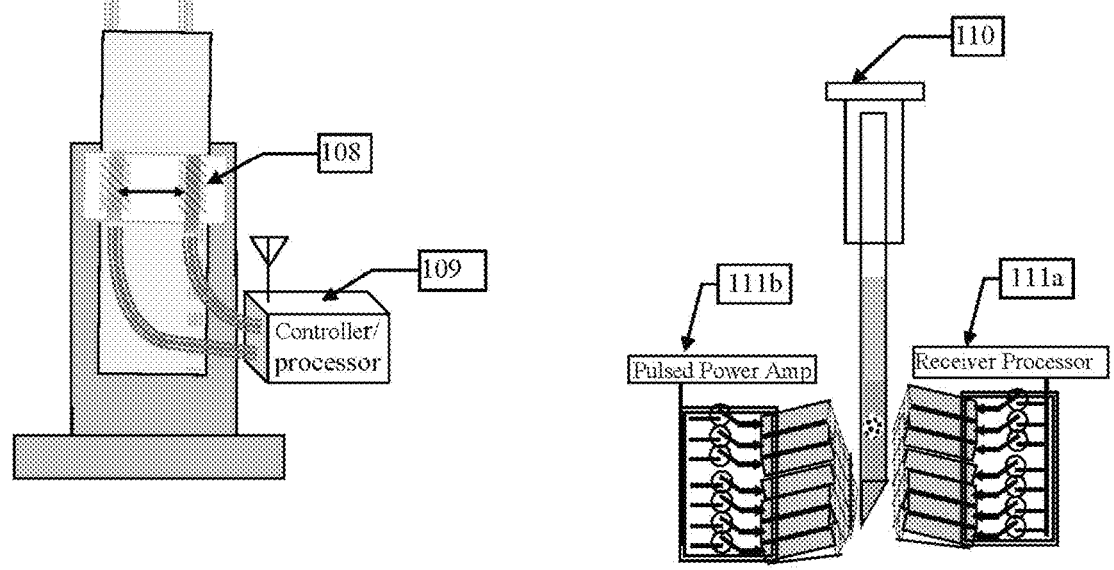
FIG. 10a illustrates the measurement of the traversal velocity of a microwave beam across a tissue sample, retrieved from the body using a syringe.

FIG. 10 illustrates three methods for measuring the traversal velocity of a microwave beam across breast tissue, two in vivo in the breast, and the third after retrieving a sample with a syringe.

In addition to the reconstructed velocity image of the breast, suspicious growths may be reexamined with a new, forceps like hinged tool, that enables to clamp the growth tissue around the tumor and measure the traversal velocity of a limited number of microwave beams across the tumor, using several mini transmitter and a mini receiver antennas, which are just miniature DRA crystals, embedded at the tips of the forceps. A similar instrument composed of two needles, one acting as a mini-transmitter and the other as a mini-receiver, enables to penetrate the breast at the sides of the suspected tumor and measure the traversal time across the tumor.

As mentioned above, traversal velocity of a sample of a body tissue is a measure of its "malignancy".

As detailed above the "traversal velocity" may be measured by the time it takes for a microwave pulse transmitted by an antenna to reach a Receiver across the sample. The, half wavelength (.lamda./2) of a Strontium Titanate crystal that has a dielectric constant .epsilon.=300 that emits a 5 GHz beam is) 1/2[(3.10.sup.10)/(17)5.10.sup.9]-1.7 mm. A DRA antenna described above in conjunction with FIG. 2 is a minuscule antenna at high microwave frequencies with very high efficiency above 95% as illustrated in the table below.

TABLE-US-00002 T.sub.R-R.sub.C Distance .lamda./2 0.1.lamda. 2-cm 1 cm 5 mm frequency SrTiO.sub.3 SrTiO.sub.3 forceps×5 GHz 1.7 mm 340.mu. twizzers×10 GHz 850.mu. 170.mu. needles×15 GHz 550.mu. 110.mu.

As the attenuation at high microwave frequencies grows exponentially, the relative advantages of high dielectric constant antennas is in measuring velocity at short distances such as the diameters of tumors that run from millimeters to centimeters. Melanomas and other malignant tumors close to the skin surface may be diagnosed with special tweezers-like mechanical tools carrying at their twin arms millimeter sized Transmitters 102a and Receivers 102b. As Dielectric Resonant Antennas have efficiencies above 95% and sub-millimeter sizes, the traversal time of a tumor may be measured with extreme efficiency by tweezers like tools. illustrated above. Skin growths and breast tumors close to the surface may be "squeezed" to make them stick-out the surface and traversal times measured through the protruding tissue. Alternatively, in breast or other soft tissue, tweezer like instruments carrying DRA antennas at their tips may be used to compress the soft tissue locally and thus reduce the path containing the suspected growth, thus enabling to measure the traversal time through the locally compressed flesh.

A twin needled syringe 107 having at the tips of the sub-millimeter cannulae, transmitter and Receiver DRAs, 106a, 106b, may be inserted onto the breast to a location previously imaged and suspected to contain malignant tissue, for confirmation purposes. In case of doubt if the location has been marked with a "marker", the measurement may be repeated at given intervals of time to check progress one way or another.

The malignancy 3a of an excised flesh or biopsized tissue, may also be checked by placing the specimen or the tube containing said specimen between a linear array of transmitters 111a and receiver DRAs 111b and the traversal times recorded along the tube, thus scanning all the tissue and determining the degree of malignancy as a function of depth.

Figure 11:
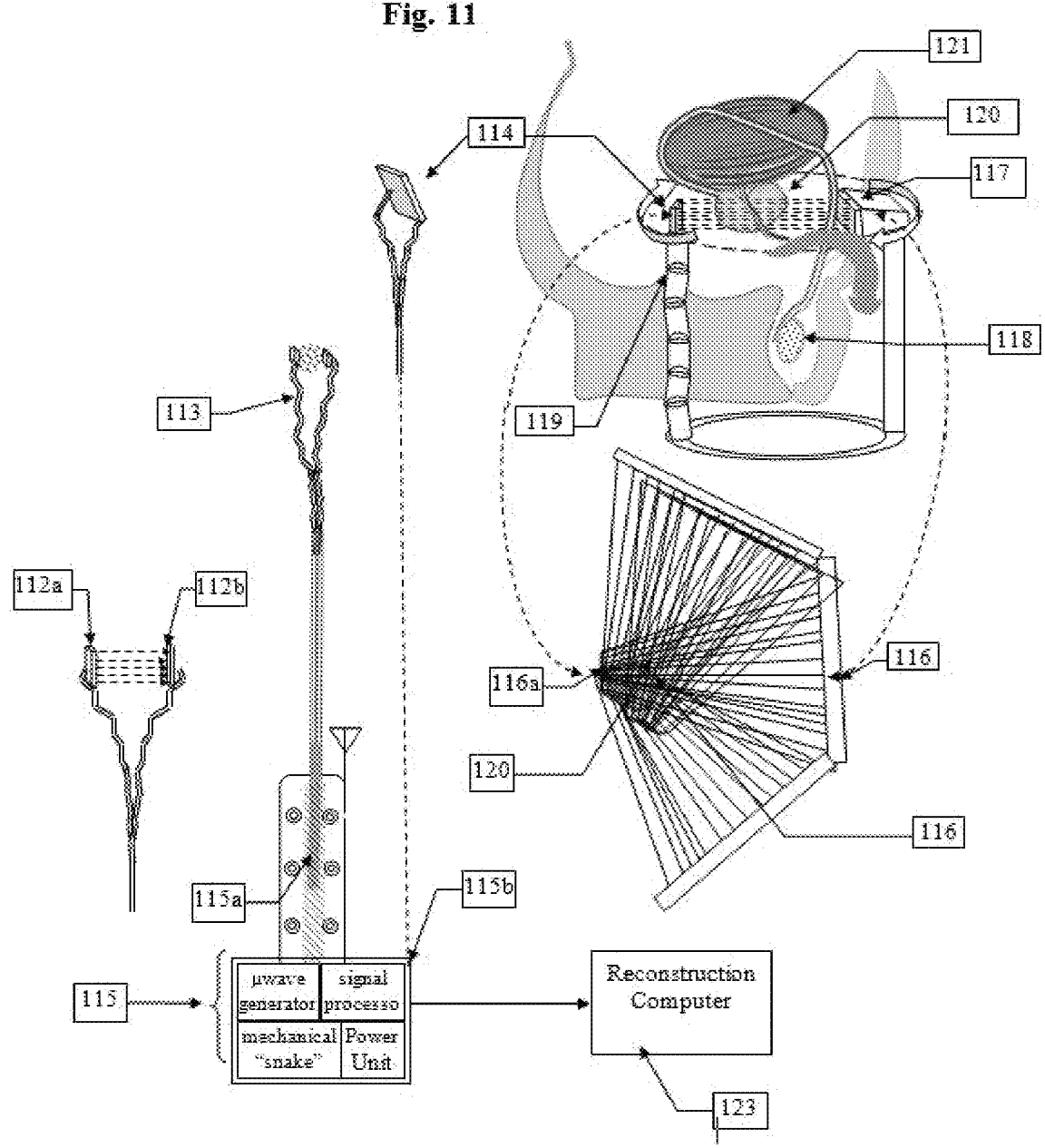
FIG. 11 illustrates an endoscopic Tomograph for measuring the traversal velocity of a prostate using a small transmitter introduced through the rectum to one side of the prostate and a large receiver at the abdomen in front of the transmitter

FIG. 11 illustrates an Endoscopy Tomograph used for "Velocity Imaging" internal body organs such as the Prostate or the Stomach. The Endoscopy Tomograph is composed of a base unit 115 including a power unit, a mechanical "snake" activator that leads the various body insertable "snake" units (112a, 112b, 113, 114) in space, by propelling them in 3D, using 6 buttons 115a, a microwave generator that feeds the transmitters and a signal processor that processes the Receiver's signals; a Reconstruction Computer 123 then builds the Velocity Images built out, of the "Rays" between the Transmitters and the Receivers which can be within or outside the body.

In the case of "Velocity Imaging" the prostate 120, a limited sized array of DRA transmitters 116a is introduced close to the prostate through the rectum and placed close to the prostate wall, while the relatively large Receiver array 117 is placed outside the body and pressed against the patient's abdomen, The transmitter and receiver arrays facing each the other, may move around the prostate gland, for as much as the body tissue around the prostate gland allows.

It is important to mention that the "Velocity Volume" of the Prostate gland, including several slices, may be reconstructed, when some Rays are obstructed by the body tissue; in this case the values of "unmeasured pixels" may be replaced by the average values of adjacent measured pixels, making the set of equations iteratively converge.

The Gleason score of Prostate Gland malignancy illustrated here shows cellular tissues as viewed under a pathology microscope and classified according to their perceived Malignancy. Structures with a multiplicity of "air-tissue" interfaces lead to multiple scatterings and therefore cause larger delays as there are more scattering events.

Figure 12:
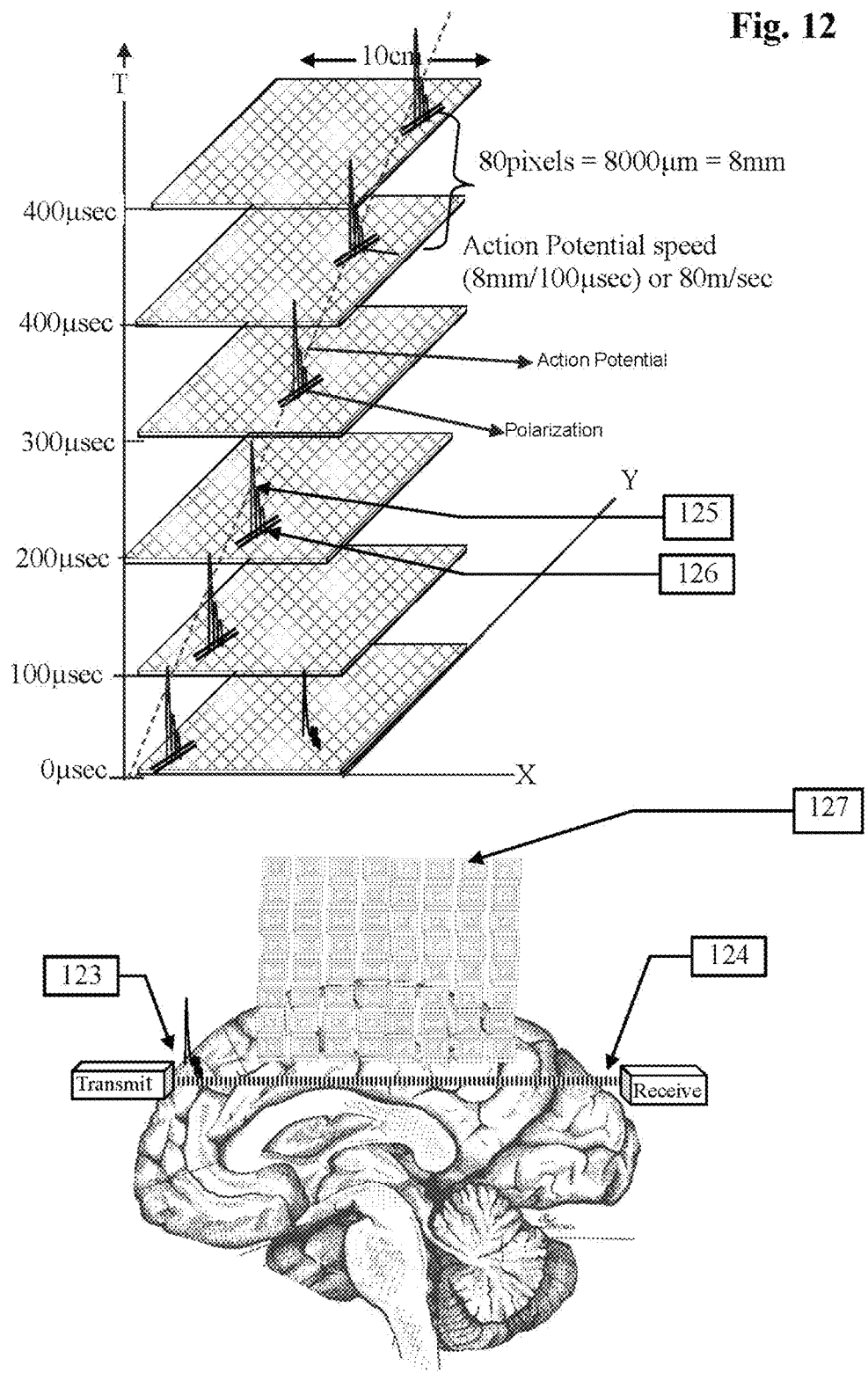
FIG. 12 illustrates the dynamic imaging of regions of the brain at millisecond time scales for functional imaging of axons.

FIG. 12 illustrates the, possible dynamic imaging of partial regions of the brain traversed by microwaves, at millisecond time scales. As an electrical communication in the brain is accompanied by a trail of polarized CSF 126 surrounding the action potential 125, and as this polarization is detectable in time scales of microseconds, it is in principle possible to image the regional states of polarization in the millisecond time scales and follow brain communications.

As explained above our system can image velocity changes at an upper section of the brain at a rate of $10^3$ frames/sec by scanning said section using transmit and receive antennas 123, 124, where a frame measures about $(10\ cm)^2$. An "Action Potential" moving, at a speed of $V=1$ m/sec, for example, will move during one frame whose duration is $100\ \mu sec$. by $100\ \mu m$, which is the length of one pixel. Thus during 1000 consecutive frames, it will move $10^3$ pixels which is the length of the slice. Thus the route of the "action potential" defined by the "change of velocity" may be followed either within the same "slice" or will "transfer" to another "slice" below or above the initial frame; knowing its origin and its repetition rate, one can reconstruct its route and its destination, in the slice or in adjacent above or slices below. Our ability to image/freeze the position of the action potential in space every millisecond will be able to differentiate one "route" from another.

An array of miniature pick-up LC coils 127 of $1\ mm^2$ each, able to identify passing electrical pulses underneath with $+-100\ \mu m$ accuracy and less than 100 picosecond time resolution, as described in connection with FIG. 9, may be placed above the route of the Axon Potentials and help confirm the "route" by coincidence, and differentiate it from other zillion signals circulating in the brain at the same time. Thus the combination of the Velocity Tomography and pick-up coils technology may be a new tool for probing the functioning of the brain.

Figure 13:
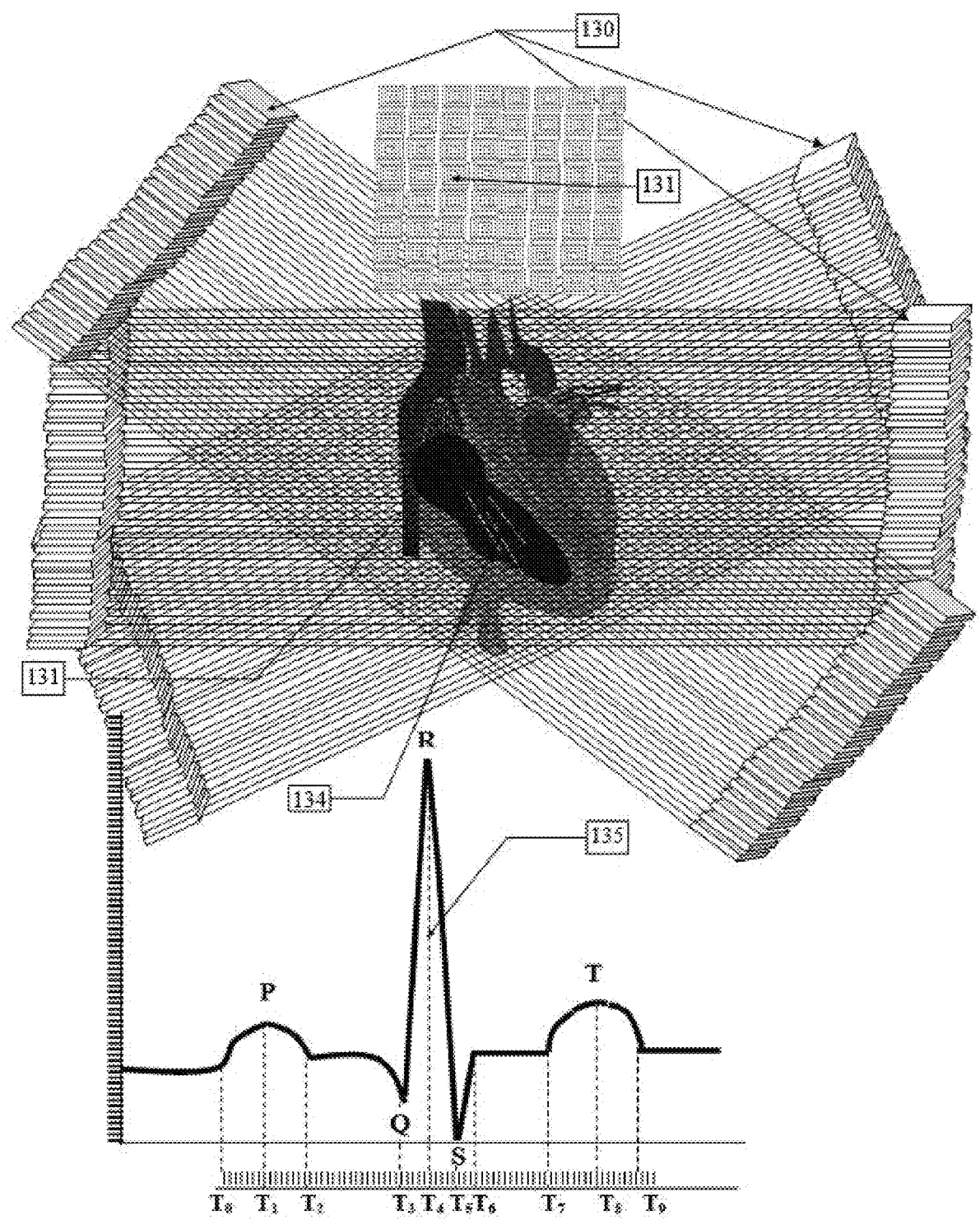
FIG. 13 illustrates the dynamic imaging of the heart in order to correlate the route of the Action Potentials with the ECG signals during a whole cycle

FIG. 13 illustrates the Velocity imaging of the heart and the ECG trace of the heart in view of imaging the correlation between the route of the Action potentials on the heart during one cycle of the beating heart, the corresponding ECG signal in the same signal, and the corresponding electrical activity on the surface of the, heart as detected on an array of microcoils covering the surface of the heart.

FIG. 14 illustrates the Velocity Imaging of Giant Cells, 140, 141. in view of identifying their malignancy, growth rate and their constitution without having to take a biopsy, which in many cases, such as the Giant Cell Arteritis, is not a simple procedure. It is expected that a non-invasive tomography will confirm or reject many hypotheses and advance the understanding of the malady.

There are multiple ways to realize the invention explained above, combining the differentiating features illustrated in the accompanying figures, and devising new embodiments of the method described, without departing from the scope and spirit of the present invention. Those skilled in the art will recognize that other embodiments and modifications are possible. While the invention has been described with respect to the preferred embodiments thereof, it will be understood by those skilled in the art that changes may be made in the above constructions and in the foregoing sequences of operation without departing substantially from the scope and spirit of the invention. All such changes, combinations, modifications and variations are intended to be included herein within the scope of the present invention, as defined by the claims. It is accordingly intended that all matter contained in the above description or shown in the accompanying figures be interpreted as illustrative rather than in a limiting sense.

The invention claimed is:

1. A method for imaging a region of the human body using transmitters and receivers of microwave rays, for determining local traversal velocity data of body parts, the method comprising:
   detecting microwave rays via a transmitter configured to emit microwave beams and a receiver configured to receive the emitted microwave beams, the transmitter and receiver positionable at traverse locations with respect to the tissue to be imaged, and
   processing said detected microwave rays by tomographically reconstructing the volume of said body parts, in terms of local velocities of each individual beam in each volumetric unit of said body part, wherein,
   said reconstruction based on the traversal times along the routes of the microwaves,
   generates a volumetric dataset with a local velocity indicated for each volumetric unit, wherein,
   the local velocities are utilized to determine the permittivity of the traversed volumetric units; and,
   providing to a display monitor, an image differentiating between tissue characteristics based on the permittivity of the traversed volumetric units along each beam.

2. A method as of claim 1 imaging a region of the human body with microwave rays, the method further comprising:
   differentiating between malignant and benign growths, whereby the differentiation between malignant and benign growths is based on the determined permittivity of the volumetric units comprising the growths, and,
   a determination as to the degree of malignancy is made as a function of both the depth and traversal velocity data of the volumetric units.

3. A method as of claim 1, for imaging the human body with microwave rays, the method further comprising:
   selecting the microwave rays half-wavelengths to be of the order of the sizes of the searched growths.

4. A method for imaging the human body with microwave rays as in claim 1, the method further comprising:
   the measurement of the time it takes to traverse body parts, is carried out by a phase-locked-loop system.

5. A method for imaging the human body with microwave rays as in claim 1, wherein said measurement comprises detecting time intervals up to a picosecond accuracy.

6. A method as in claim 1, further comprising:
   imaging the volume of a pendant Breast, by traversing consecutive slices, each slice from multiple levels and directions, using arrays of transceivers around the periphery of said pendant breast, wherein said multiplicity of transceivers generate rays having traversal velocity values across substantially all voxels of the pendant breast, and wherein the values of non-traversed voxels may be replaced by the average values of adjacent traversed pixels voxels and wherein an iterative mathematical Reconstruction algorithm, calculates the local traversal velocities in 3 dimensions across all voxels of the Pendant Breast.

7. The method as of claim 1, further comprising:
the positioning of at least one transmitter and at least one receiver in traverse locations with respect to a small tissue volume, for measuring the time elapsed between emission of the signal from said transmitter and receipt of the signal at said receiver.

8. The method according to claim 1, further comprising:
the traversal time increase in a traversed tissue without clear borders is indicative of local malignancy fed by an Angiogenesis process.

9. The method according to claim 1, further comprising:
repeating the transmitter signal multiple times, sufficient to increase the cumulative number of photons that trigger the receiver sensor.

10. The method according to claim 1 further comprising,
A display monitor for displaying the Tomographically reconstructed map, showing the black-to-white grading of the calculated local velocities through the displayed tissue.

11. The method according to claim 1, wherein,
said Tomographic Reconstruction process comprises applying a "randomized Kaczmarz" algorithm to said velocity measurements.

12. The method according to claim 1, comprising
generating dynamic imaging of routes of "action potentials" propagating within the heart, using transmitters and receivers of different wavelengths and correlating said routes with "ECG" signals.

13. The method according to claim 1, comprising
generating dynamic imaging of routes of "action potentials" propagating within the Brain using transmitters and receivers of different wavelengths and correlating said routes with Brain signals.

14. An apparatus for linear velocity imaging Tomography of a tissue volume, comprising:
at least one transmitter configured to emit a microwave beam and
at least one receiver configured to receive the emitted microwave beams; wherein,
the receiver and transmitter are positionable at traverse locations with respect to the tissue to be imaged and,
a processor configured to measure the traversal time of each beam between the emission and reception of the beam(s) using differential time measurements at sub-wavelength accuracies, and,
a tomograph comprising: a reconstruction computer, configured to reconstruct the tissue volume in terms of velocities of the beams in each volumetric unit of said tissue, using the elapsed traversal times and the routes of the of the microwave beams, thereby generating a volumetric data set with a velocity for each volumetric unit as well as the processing of local velocity data and,
a display monitor configured to display an image, differentiating between tissue characteristics based on the displayed permittivity of the traversed volumetric units along each beam.

15. An apparatus according to claim 14, wherein,
the malignancy of a biopsy tissue specimen, excised from a body, through a needle, is ascertained by placing said needle containing said specimen, between the transmitter and receiver of a device, and wherein,
said device together with the tomograph, are configured to record the traversal times of the microwaves along the length of the needle, and output the degree of malignancy as a function of both the depth and traversal velocity of the volumetric units along the length of the needle.

16. An apparatus for imaging a region of the human body with microwave rays, for obtaining traversal velocity maps of body structures as in claim 14 wherein,
the routes of Action Potentials propagating within the nerves in the brain may be followed by tracking the electrical polarization changes outside the nerves, wherein,
dynamic imaging of a section of the brain, may be velocity mapped, showing the changing local polarization from one slice to the next, as the Action Potentials move from one place to another in the brain, wherein,
the traversal velocity maps will show the local polarization signature moving within a map of a slice of the brain, and wherein,
dynamic imaging of a section of the brain velocity mapped, will show the changing local polarization in sequences of slices depending on the speed of the Action Potentials and wherein,
the speed of a specific action potential calculated from its position in a sequence of slices, serves to differentiate it from other Action Potentials that may be circulating on said section of the brain at the same time, and wherein,
the probable direction of an Action Potential is deducted from its position in the initial slices, and the direction of the imaged slice of the brain scan may be changed by starting a new scan in a new direction, wherein,
the entire route of the action potential which most probably is not linear, may be followed sequentially, from its start to its destination.

17. An apparatus for imaging a region of the human body with microwave rays, for obtaining traversal velocity maps of body structures as in claim 14, wherein,
a helmet-like Velocity Tomograph, to be worn by patients suspected to have had an Hemorrhagic "stroke" for imaging the brain, is tuned to show the large blood pool section of the image, wherein,
said helmet like enclosure houses a circular array of microwave transceivers situated around a pouch of fluid that separates the user's head from the transmitters, wherein,
said fluid pouch has an intermediate dielectric constant, between that of the skull on one side and that of the transceivers on the other side, and wherein,
the dynamic Velocity Imaging of large delays, will show the blood arteries as a function of time, above the CSF pool, over the background images of the white and gray brains.

18. An apparatus for imaging a region of the human body with microwave rays, for obtaining traversal velocity maps of body structures as in claim 14 wherein,
the section of the human body to be examined for malignancy is limited in size, and accessible from outside the body squeezing the surrounding tissue, wherein,
an array of mini-transceivers appended to the extremities of a "forceps-like" hinged tool, that enables to clamp said body tissue, and transmit the microwave beams one-at a-time, through it, receive and transmit them through the "hands" of the forceps-like tool, and wherein, a processor linked to the forceps-like tool, measures the elapsed time between the transmitters and receivers of the tool and conveys the data to a Reconstruction computer wherein, the procedure of determining the traversal time is repeated from several directions using the forceps like tool, to grab and squeeze said body tissue and transmit the traversal data to the external processor that analyses said data and determines its degree of malignancy from several directions.

19. An apparatus for imaging a region of the human body with microwave rays, for obtaining traversal velocity maps of body structures as in claim 14, wherein, a body microwave Tomograph of variable opening, for one of head, new-borns and young children, comprising multi section, multi-slice, circular DRA transmitters and receivers, wherein, said multi-section, multi-slice Tomograph consists of several movable sections that touch their adjacent sections, forming a circular opening, with DRA transceivers around said opening and wherein, said separate sectors may serve to scan a circular opening of a desired diameter, while sections covering smaller angular sections, move circularly, scanning the desired angle, in tandem with its counterpart section of transceivers, wherein, each angular section may comprise rows of DRA transceivers that may be activated one-row-at-a-time, and wherein, the sequential rows of transceivers are separated, each from-the-other, dictated by their sizes and wherein, the entire gantry of transceivers may moved along its axis, for a distance smaller than the distance between the rows of affixed transceivers and, the scan by the entire gantry of transceivers repeated, thus enabling to scan "intermediate slices".

\* \* \* \* \*